US010479748B2

United States Patent
Lapkin et al.

(10) Patent No.: US 10,479,748 B2
(45) Date of Patent: Nov. 19, 2019

(54) OXIDATION OF C1-9-ALKANES

(71) Applicant: Cambridge Enterprise Limited, Cambridge (GB)

(72) Inventors: Alexei Lapkin, Cambridge (GB); Samson Aworinde, Cambridge (GB); Kun Wang, Bridgewater, NJ (US)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 16/205,521

(22) Filed: Nov. 30, 2018

(65) Prior Publication Data

US 2019/0161423 A1 May 30, 2019

Related U.S. Application Data

(60) Provisional application No. 62/592,825, filed on Nov. 30, 2017.

(51) Int. Cl.
*C07C 29/17* (2006.01)
*C07C 29/52* (2006.01)
*C07C 45/33* (2006.01)
*C07C 27/12* (2006.01)

(52) U.S. Cl.
CPC ............ *C07C 29/172* (2013.01); *C07C 27/12* (2013.01); *C07C 29/52* (2013.01); *C07C 45/33* (2013.01)

(58) Field of Classification Search
CPC ....... C07C 29/172; C07C 27/12; C07C 29/52; C07C 45/33
USPC ........................................................ 568/912
See application file for complete search history.

(56) References Cited

U.S. PATENT DOCUMENTS

| 3,109,864 A | 11/1963 | Fox et al. |
| 3,238,238 A | 3/1966 | McNamara |
| 3,243,449 A | 3/1966 | Winnick |
| 3,375,265 A | 3/1968 | Fetterly et al. |
| 3,384,672 A | 5/1968 | Illingworth |
| 3,410,913 A | 11/1968 | McMahon, Jr. et al. |
| 3,415,621 A | 12/1968 | Gilderson et al. |
| 3,419,615 A | 12/1968 | Inchalik et al. |
| 3,442,959 A | 5/1969 | Sugerman |
| 3,454,617 A | 7/1969 | Manfred et al. |
| 3,488,740 A | 1/1970 | Russell |
| 3,524,891 A | 8/1970 | Cahn |
| 3,592,859 A | 7/1971 | Marcell et al. |
| 3,651,153 A | 3/1972 | Strauss et al. |
| 3,655,769 A | 4/1972 | McMahon |

(Continued)

OTHER PUBLICATIONS

Sakaguchi, H., E. Niki, and Y. Kamiya. 1975. "Catalytic Decomposition of T-Butyl Hydroperoxide over Boron Trioxide under Vacuum." Nippon Kagaku Kaishi, No. 4: 596-601.

(Continued)

*Primary Examiner* — Deborah D Carr
(74) *Attorney, Agent, or Firm* — Greer, Burns & Crain, Ltd.

(57) ABSTRACT

A method for the oxidation of $C_{1-9}$-alkanes including providing a mixture of a $C_{1-9}$-alkane in a liquid phase, a boron containing reagent, a free radical initiator, and a drying means, and performing an oxidation reaction at a temperature from 130° C. to 180° C. in the presence of oxygen. The drying means may be a drying agent such as a molecular sieve, or a membrane. Also a composition for oxidation of $C_{1-9}$-alkanes to sec-$C_{1-9}$-alcohols.

27 Claims, 11 Drawing Sheets

(56) References Cited

U.S. PATENT DOCUMENTS 3,832,363 A     8/1974    Fetterly et al.
3,948,992 A     4/1976    McMahon

OTHER PUBLICATIONS

Sakaguchi, H., E Niki, and Y. Kamiya. 1976. "Decomposition of Hydroperoxides by Boric Acid Anhydride in Solution. Electrophilic Hydroxylation of the Solvent." J. Chem. Soc., Perkin Trans. II 3: 855-58.

Sheldon, R.A., and J.A. van Doorn. 1974. "Boron-Catalysed Epoxidation of Olefins with Tert-Butyl Hydroperoxide." J. Catal. 34: 242-45.

Sivaev, I.B., and V.I. Bregadze. 2014. "Lewis Acidity of Boron Compounds." Coord. Chem. Rev. 270: 75-88.

Smith, J.R.L., Y. Iamamoto, and F.S. Vinhado. 2006. "Oxidation of Alkanes by Iodosylbenzene (PhIO) Catalysed by Supported Mn(III) Porphyrins: Activity and Mechanism." J. Mol. Catal. A: Chemical 252 (1-2): 23-30.

Sokova, K.M., G.A. Zelenaya, and A.N. Bashkirov. 1976. "Oxidation of Cyclododecene with Molecular Oxygen in the Presence of Boric Acid." Neftekhimiya 16 (3): 445-51.

Suresh, A.K, M.M. Sharma, and T.S. Sridhar. 2000. "Engineering Aspects of Industrial Liquid-Phase Air Oxidation of Hydrocarbons." Ind. Eng. Chem. Res. 39 (11): 3958-97.

Teles, J.H., I. Hermans, G. Franz, and R.A. Sheldon. 2015. "Oxidation." Ullmann's Encyclopedia of Industrial Chemistry. Wiley-VCH Verlag GmbH & Co. KGaA, Weinheim.

Thomas, J.M., R. Raja, G. Sankar, and R.G. Bell. 1999. "Molecular-Sieve Catalysts for the Selective Oxidation of Linear Alkanes by Molecular Oxygen" Nature 398: 227-30.

Twigg, G.H. 1954. "The Mechanism of Liquid-Phase Oxidation." Chem. Eng. Sci. Suppl. 3: 5-16.

Wolf, P.F., and R.K. Barnes. 1969. "The Borate Ester Induced Decomposition of Alkyl Hydroperoxides. The Epoxidation of Olefins by Electrophilic Oxygen." J. Org. Chem. 34 (11): 3441-45.

Wolf, P.F., J.E. McKeon, and D.W. Cannell. 1975. "Mechanisms of the the Borate Ester Induced Decomposition of Alkyl Hydroperoxides." J. Org. Chem. 40: 1875-82.

Woods, W.G., and R.J. Brotherton. 1970. "Oxidations of Organic Substrates in the Presence of Boron Compounds." In Progress in Boron Chemistry, edited by R.J. Brotherton and H. Steinberg, vol. 3, 1-115. Pergamon Press, Oxford, UK.

Zazhigalov, V.A., J. Haber, J. Stoch, B.D. Mikhajluk, A.I. Pyatnitskaya, G.A. Komashko, and I.V. Bacherikova. 1996. "A Novel Route in Partial Oxidation of N-Pentane over the VPO Catalysts: Formation of Citraconic Anhydride." Catal. Letters 37 (1-2): 95-99.

Zenker, W. 1975. "Infrared Method for the Direct Control of Paraffin-Wax Oxidation in the Presence of Boric Acid." Fette, Seifen, Anstrichm. 77 (6): 221-24.

Alagy, J., P. Trambouze, and H. Van Landeghem. 1974. "Designing a Cyclohexane Oxidation Reactor." Ind. Eng. Chem. Proc. Des. Dev. 13 (4): 317-23.

Arpentiner, P. 2006. "Synthesis of Intermediates for the Petrochemical Industry: Oxidation Processes in Liquid Phase with Oxygen." In Encyclopaedia of Hydrocarbons vol. II: Refining and Petrochemicals, edited by C. Giavarini and F. Trifiro, 636-60. Roma: ENI: Istituto Della Enciclopedia Italiana.

Balkus, K.J., M. Eissa, and R. Levado. 1995. "Oxidation of Alkanes Catalyzed by Zeolite-Encapsulated Perfluorinated Ruthenium Phthalocyanines." J. Am. Chem. Soc. 117 (43): 10753-54.

Bartoli, J.F., O. Brigaud, P. Battioni, and D. Mansuy. 1991. "Hydroxylation of Linear Alkanes Catalysed by Iron Porphyrins: Particular Efficacy and Regioselectivity of Perhalogenated Porphyrins." J. Chem. Soc., Chem. Commun. 0: 440-42.

Bashkirov, A.N., and V.V. Kamzolkin. 1959. "Synthesis of Higher Aliphatic Alcohols by Direct Oxidation of Paraffinic Hydrocarbons." In Proc. 5th World Pet. Cong., Sec. IV, Paper 15, 175-183. New York: World Petroleum Cogress.

Bashkirov, A.N., V.V. Kamzolkin, K.M. Sokova, T.P. Andreyeva, V.V. Komeva, and L.I. Zakharkin. 1961. "The Production of Cyclododecanol by the Liquid-Phase Oxidation of Cyclododecane." Neffekhimiya 1 (4): 527-34.

Bashkirov, A.N., V.V. Kamzolkin, K.M. Sokova, and T.P. Andreyeva. 1965. "The Mechanism of the Liquid-Phase Oxidation of Paraffinic Hydrocarbons." In the Oxidation of Hydrocarbons in the Liquid Phase, edited by N.M. Emanuel', 183-93. Oxford: Pergamon Press Ltd.

Bateman, L. 1954. "Olefin Oxidation." Q. Rev. Chem. Soc. 8: 147-67.

Beckettt, M.A., M.P. Rugen-Hankey, G.C. Strickland, and K.S. Varma. 2001. "Lewis Acidity in Haloalkyl Orthoborate and Metaborate Esters." Phosphorus, Sulfur Silicon Relat. Elem. 169 (1): 113-16.

Beckett, M.A., G.C. Strickland, J.R. Holland, and K.S. Varma. 1996. "A Convenient N.M.R. Method for the , Measurement of Lewis Acidity at Boron Genres: Correlation of Reaction Rate of Lewis Acid Inititated Epoxide Polymerizations with Lewis Acidity." Polymer 37 (20): 4629-31.

Bigot, J.A., P.L. Kerkhoffs, and H. Theeuwen. 1965. "On the Liquid Phase Air Oxidation of N-Heptane." Recl. Trav. Chim. Pays-Bas 84 (10): 1243-46.

Boss, B.D., and R.N. Hazlett. 1969. "Oxidation of Hydrocarbons in the Liquid Phase: N-Dodecane in a Borosilicate Glass Chamber at 200° C." Can. J. Chem. 47 (22): 4175-82.

Boss, B.D., and R.N. Hazlett. 1975. "N-Dodecane Oxidation—Elucidation by Internal Reference Techniques." Ind. Eng. Chem. Prod. Res. Dev. 14 (2): 135-38.

Bridger, R.F., A.L. Williams, and L.J. McCabe. 1966. "Antioxidant Reactions of 10-Hydroxy-10,9-Boroxarophenanthrene." Ind. Eng. Chem. Prod. Res. Dev. 5 (3): 226-30.

Brioch, F. 1962. "Oxydationsreaktionen in Der Petrochemie." Chem. Ing. Tech. 34: 45-61.

Brown, D.M., and A. Fish. 1969. "The Extension to Long-Chain Alkanes and to High Temperatures of the Hydroperoxide Chain Mechanism of Autoxidation." Proc. Roy. Soc. Lond. Ser. A. 308: 547-68.

Centi, G., J. Lopez-Nieto, D. Pinelli, and F. Trifirò. 1989. "Synthesis of Phthalic and Maleic Anhydrides from N-Pentane. 1. Kinetic Analysis of the Reaction Network." Ind. Eng. Chem. Res. 28 (4): 400-406.

Costas, M. 2011. "Selective C—H Oxidation Catalyzed by Metalloporphyrins." Coord. Chem. Rev. 255 (23-24): 2912-32.

De Klerk, A. 2003. "Continuous-Mode Thermal Oxidation of Fischer-Tropsch Waxes." Ind. Eng. Chem. Res. 42: 6545-48.

Emanuel, N.M. 1974. "Kinetics and Mechanism of Chain Reactions of Liquid-Phase Oxidation of Hydrocarbons." Izv. Akad. Nauk SSSR, Ser. Khim. 5: 1010-23.

Griesbaum, K., A. Behr, D. Biedenkapp, H-W. Voges, D. Garbe, C. Paetz, G. Collin, D. Mayer, and H. Hoke. 2012. "Hydrocarbons." Ullmann's Encyclopedia of Industrial Chemistry. Wiley-VCH Verlag GmbH & Co. KGaA, Weinheim.

Hartmann, M., and S. Ernst. 2000. "Selective Oxidations of Linear Alkanes with Molecular Oxygen on Molecular Sieve Catalysts—A Breakthrough?" Angew. Chem. Int. Ed. 39 (5): 888-90.

Holcik, J., J.L. Koenig, and Jr. Shelton. 1983. "The Antioxidant Activity of Phosphorus Compounds. Part I: Decomposition of Hydroperoxides by Pentaerythritol Diphosphites." Polym. Degrad. and Stab. 5: 373-97.

Ingold, K.U. 1961. "Inhibition of the Autoxidation of Organic Substances in the Liquid Phase." Chem. Rev. 61 (6): 563-89.

Itskovich, V.A., P. Lak Von, T.G. Maslayanskaya, L.P. Tsudikova, and V.V. Fokin. 1978. "Oxidation of Naphthene Hydrocarbons in the Presence of Boron Compounds." Neftekhimiya 18 (4): 603-8.

Jevtic, R., P.A. Ramachandran, and M.P. Dudukovic. 2009. "Effect of Oxygen on Cyclohexane Oxidation: A Stirred Tank Study." Ind. Eng. Chem. Res. 48 (17): 7986-93.

Kamzolkin, V.V., A.N. Bashkirov, M.I. Khotimskaya, N.M. Grozhan, and G.M. Yezhenkina. 1961. "Synthesis of C6- C10 Aliphatic Alcohols by the Liquid-Phase Oxidation of Alkanes under Pressure" Neftekhimiya 1: 244-54.

Kerr, J.A. 1966. "Bond Dissociation Energies by Kinetic Methods." Chem. Rev. 66 (465-500).

(56) References Cited

OTHER PUBLICATIONS

Kijenski, J., and A. Baiker. 1989. "Acidic Sites on Catalyst Surfaces and Their Determination." Catal. Today 5 (1): 1-120.

König, T., D. Männel, W. D. Habicher, and K Schwetlick. 1988. "Organoboron Antioxidants: Part 1. Boric Acid Derivatives as Primary Antioxidants." Polym. Degrad. And Stab. 22: 137-45.

König, T., W.D. Habicher, and K Schwetlick. 1989. "Organophosphorus Antioxidants. X. The Hydroperoxide Decomposing Action of Phosphites, Phosphonites and Thiophosphites." J. Prakt. Chem. 331 (6): 913-22.

Korili, S.A., P. Ruiz, and B. Delmon. 1996. "Oxidative Dehydrogenation of N-Pentane on Magnesium Vanadate Catalysts." Catal. Today 32: 229-35.

Kunzelmann, A., G. Lauterbach, V.M. Potekhin, W. Pritzkow, W. Schmidt-Renner, and L.F. Vasina. 1986. "On the Mechanism of Hydroperoxide Decomposition by Boric Acid Derivatives." J. Prakti. Chemie 328 (5-6): 772-76.

Kurata, N., K. Koshida, and M. Tsuchino. 1992. "Synthesis of S-Alcohols via Liquid Phase Oxidation of N-Paraffins: Effects of Ammoniac Base Co-Catalysts." J. Jpn. Oil Chem. Soc. 41 (12): 1203-9. Chapter 5. Kinetic study of boron-assisted liquid-phase oxidation of n-pentane 45.

Lappe P. and T. Hofmann. 2011. "Pentanols." Ullmann's Encyclopaedia of Industrial Chemistry. Weinheim: Wiley-VCH Verlag GmbH & Co. KGaA.

Lappert, M.F. 1956. "Organic Compounds of Boron." Chem. Rev. 56 (5): 959-1064.

Lappert, M.F. 1958a. "Cyclic Organic Boron Compounds. Part I. Preparation, Characterisation, and Stability of Esters of Metaboric Acid." J. Chem. Soc., No. 2790: 2790-93.

Lappert, M.F. 1958b. "Cyclic Organic Boron Compounds. Part II. Chemical Properties of N-Butyl Metaborate." J. Chem. Soc., 3256-59.

Labinger, J.A., and J.E. Bercaw. 2002. "Understanding and Exploiting C—H Bond Activation." Nature 417 (6888): 507-14.

Lauterbach, G., W. Pritzkow, T.D. Tien, and V. Voerckel. 1988. "Studies on the Decomposition of Alkyl Hydroperoxides by Different Catalysts." J. Prakt. Chemie 330 (6): 933-46.

Lee, K.W., M.J. Choi, and S.B. Kim. 1987. "Liquid-Phase Oxidation of N-Dodecane in the Presence of Boric Acid." Ind. Eng. Chem. Res. 26: 1951-55.

Lyons, J.E., P.E. Ellis Jr., and H.K. Myers. 1995. "Halogenated Metalloporphyrin Complexes as Catalysts for Selective Reactions of Acyclic Alkanes with Molecular Oxygen." J. Catal. 155 (1): 59-73.

Mishra, G.S., and A.J.L. Pombeiro. 2006. "Oxyfunctionalization of N-Pentane and N-Hexane by Oxovanadium Complexes Supported on Carbamated Modified Silica Gel" Appl. Catal. A: Gen. 304: 185-94.

Modën, B., Bi-Z. Zhan, J. Dakka, J.G. Santiesteban, and E. Iglesia. 2007. "Reactant Selectivity and Regiospecificity in the Catalytic Oxidation of Alkanes on Metal-Substituted Aluminophosphates." J. Phys. Chem. C 111 (3): 1402-11.

Mushenko, D.V., and R.D. Dergacheva. 1961. "The Production of Secondary Amyl Alcohols." Neftekhimiya 1 (6): 811-16.

Novak, F.I., V.V. Kamzolkin, Y.A. Talyzenkov, and A.N. Bashkirov. 1967. "Mechanism of the Effect of Boric Acid on Liquid-Phase Oxidation of Paraffin Hydrocarbons." Neftekhimiya 7 (2): 248-53.

Puring, M.N., V.M. Poteckhin, V.A. Itskovich, and V.B. Lebedev. 1975. "Complex Formation of 1-Methylcyclohexylhydroperoxide with Esters of Boric Acid." Zhurnal Prikladnoi Spektrospii 22 (2): 271-75.

Roduner, E., W. Kaim, B. Sarkar, V.B. Urlacher, J. Pleiss, R. Glaser, W-D. Einicke, et al. 2013. "Selective Catalytic Oxidation of C—H Bonds with Molecular Oxygen." ChemCatChem 5 (1): 82-112.

Sakaguchi, H., Y. Kamiya, and N. Ohta. 1972. "Autoxidation of Hydrocarbons in the Presence of Boric Acids Decomposition of Aromatic Hydroperoxides." Bull. Jap. Pet. Inst. 14 (1): 71-75.

OXIDATION OF C1-9-ALKANES

CROSS REFERENCE TO RELATED APPLICATIONS

This application claims priority to U.S. Provisional Patent Application No. 62/592,825 filed on Nov. 30, 2017, the entirety of which is hereby incorporated by reference.

FIELD OF THE INVENTION

The present invention relates to the oxidation of alkanes and specifically to the oxidation of $C_{1-9}$-alkanes. The present invention provides a method for the oxidation of $C_{1-9}$-alkanes to alcohols using a boron containing reagent.

BACKGROUND $C_{1-9}$-Alkanes, such as n-pentane, are a major component of the naphtha cut i.e. the gasoline fraction from petroleum refining. However, these short chain alkanes are currently not particularly well utilized in the petrochemical industry as a raw material for the production of useful chemicals.

There is considerable interest from the petrochemical industry in a process that can be applied for the upgrading and conversion of these low-cost, low-value hydrocarbon feedstock into chemicals and intermediates of higher commercial value.

Currently in the petrochemical industry, n-pentane is mostly processed by steam cracking at high temperatures to make olefins (Matar and Hatch 2000). However, this process is highly endothermic, requiring temperatures in the range of 500 to 800° C. to drive the reactions towards olefins, and is therefore very energy intensive.

Alcohols are valuable chemical products and intermediates. For example, sec-pentanols are industrially valuable chemicals that are used as solvents for paints, lacquers and varnishes, largely in the form of sec-amyl acetates (Weissermel and Arpe 1997; Lundeen and Poe 1977). They are also widely used as flavoring agents for perfumes in the fragrance industry, in the manufacture of flotation agents for non-ferrous ores in the mining industry and for the extraction of penicillin from corn-steep liquor in the pharmaceutical industry. As chemical intermediates they are used as precursors in the synthesis of other chemicals such as higher boiling esters, which find uses as plasticizers.

As such, methods to produce sec-pentanol and other short chain alcohols on an industrial scale directly from the corresponding short chain alkanes are desirable.

Secondary pentanols are currently manufactured on a large scale by the hydration of 1- and 2-pentenes with >80% concentrated sulfuric acid. The sulfuric acid pentyl esters formed are subsequently hydrolyzed to yield 2- and 3-pentanols, followed by fractional distillation for separation and purification (Lappe and Hofmann 2011; Mushenko and Dergacheva 1961). The process of hydration of olefins to secondary alcohols with sulfuric acid has been known for a long time.

One alternative process is the direct oxidation of short chain alkanes, such as n-pentane, into oxygenated products, such as alcohols and ketones. Despite the potential economic value of this approach, there are currently no practical industrial applications of this route for the conversion of short chain alkanes.

The conversion of short chain alkanes to useful chemicals by direct oxidation with molecular oxygen in the liquid phase is a significant challenge for a number of reasons. One of the main issues with the activation of short chain alkanes, is their stability and low reactivity (Shilov and Shul'pin 2000). Short chain alkanes are considerably more difficult to oxidize than longer chain alkanes as shown in Table 1, the order of reactivity correlating with decreasing C—H bond strengths as chain length increases (Teles et al. 2015; Freund et al. 1982).

TABLE 1

Relative oxidation rates of different linear alkanes.

| n-Alkane | Relative oxidation rate $\text{Oxidation rate} = \dfrac{\text{mol } O_2}{(\text{mol alkane}) \times \text{time}}$ |
|---|---|
| Ethane | 0.001 |
| Propane | 0.1 |
| Butane | 0.5 |
| Pentane | 1.0 |
| Hexane | 7.5 |
| Octane | 200 |
| Decane | 1380 |

As a result of their relatively low reactivity compared to longer chain alkanes, the oxidation of short chain alkanes under typical conditions of liquid-phase reactions results in conversion rates that are too low for commercial exploitation.

Another problem is that the oxidation process is typically limited by poor selectivity to alcohols. Selectivity is challenging for two reasons.

First, the free radical autoxidation process is indiscriminate, with oxidative attack on all reactive C—H groups in the alkane molecule. Consequently, for alkanes with more than four carbon atoms such as n-pentane, a complex mixture of oxygenated products, including hydroperoxides, alcohols, ketones, carboxylic acids, and esters, with all possible isomers is formed. It is possible to obtain high selectivity, especially at low conversions, in the case of simple hydrocarbon molecules containing only one type of reactive C—H group, such as cyclohexane.

A second and more general problem with achieving high selectivity to alcohols is that the alcohols themselves are intermediate products, which are far more reactive than the alkane starting material, and are thus more readily overoxidized into by-products such as ketones and acids. Hence the oxidation process generally offers little control over alcohol selectivity (Labinger and Bercaw 2002).

A number of approaches for the direct oxidation of longer chain alkanes (i.e. alkanes with a carbon chain length of 10 or more) to selectively give sec-alcohols are known and used industrially. These include metal catalyzed direct oxidation and direct oxidation in the presence of boron containing reagents.

The liquid-phase oxidation of hydrocarbons in the presence of boron compounds has been known for over five decades (Woods and Brotherton 1970). This approach was first developed in the late 1950s by Bashkirov et al. for the oxidation of long chain alkanes. Bashkirov showed that paraffins such as n-tridecane ($C_{13}H_{28}$) and n-hexadecane ($C_{16}H_{34}$) can be oxidized with an oxidizing gas containing 3 to 3.5% oxygen at 165 to 170° C. with 5 wt % boric acid (Bashkirov et al. 1965; Bashkirov and Kamzolkin 1959). High selectivity to alcohols was reported compared with oxidations without boric acid.

Boron promoted oxidation of alkanes received considerable attention in the 1960s and 1970s. The boron catalyzed oxidation process has been applied to the oxidation of $C_{10}$-$C_{20}$ alkanes for the synthesis of higher aliphatic alcohols used in the manufacture of detergents and surfactants (Griesbaum et al. 2012, Encyclopaedia of Industrial Chemistry; Arpentinier 2006, Encyclopaedia of Hydrocarbons; Weissermel and Arpe 1997, Industrial Organic Chemistry).

One commercial application that does not involve a long chain alkanes is the oxidation of cyclohexane. In cyclohexane all carbon atoms are equivalent and so cyclohexane is not representative of short chain alkanes. Further the oxidation of cyclohexane does not show high selectivity for the alcohol product. The product of the process comprises a mixture of cyclohexanol and cyclohexanone.

It is proposed that the boron containing reagent traps the alcohol when it is formed in the reaction mixture to give a borate ester. Water produced during the reaction is driven off as steam due to the high reaction temperatures employed. This effectively blocks the further oxidation from the alcohol. It is also proposed that the boron containing reagent reduces reaction rate and conversion by promoting heterolytic decomposition of the intermediate alkyl hydroperoxides.

Despite successful implementation of the boron-promoted oxidation process with long-chain alkanes and cycloalkanes, there has been no reported study of this concept applied to the oxidation of short-chain alkanes, such as n-pentane.

It is evident that the direct oxidation of short chain alkanes to alcohols with high selectivity is a difficult problem for a number of reasons such as the low reactivity and low boiling point of the alkanes. Despite approaches that have been reported for longer chain alkanes and have been known for many years, the issue of conversion and selectivity for short chain alkanes still remains largely unsolved.

The present invention aims to solve one or more of the problems associated with oxidation of short chain alkanes to alcohols such as secondary alcohols (sec-alcohols).

SUMMARY OF THE INVENTION

In a general aspect the invention provides a method for the oxidation of $C_{1-9}$-alkanes to $C_{1-9}$-alcohols.

The method of the invention provides an industrially viable process with good selectivity for alcohol products, for example, good selectively for sec-alcohols. As discussed above, it is desirable to provide such selective processes for shorter chain alkanes as such methods have long been unavailable for industrial processing of such alkanes.

In one aspect of the invention there is provided a method for the oxidation of $C_{1-9}$-alkanes. The method comprises providing a mixture of a $C_{1-9}$-alkane in the liquid phase, a boron containing reagent, a free radical initiator and a drying means at a temperature from 130° C. to 180° C. in the presence of oxygen. The mixture is at a pressure suitable to maintain the alkane in the liquid phase, for example, the pressure may be from 2 to 5 MPa (i.e. 20 to 50 bar).

Without wishing to be bound by theory, it is proposed that the alcohol formed in the reaction is trapped by the boron containing reagent by (trans)esterification to give a borate ester in solution. The drying means prevents decomposition of the borate ester by sequestering water that is produced in the reaction, which means it is subsequently unavailable to react with the borate ester. The boron species also promotes selective decomposition of the intermediate alkyl hydroperoxides to the corresponding alcohol. This heterolytic decomposition effectively terminates the radical chain reaction and reduces the reaction rate and conversion of the process. The radical initiator initiates further radical formation to compensate the reduction in rate and conversion.

In this way the method of the present invention provides a selective oxidation of $C_{1-9}$-alkanes to alcohols with industrially viable yields. This method also provides simple reaction conditions that can be readily used on an industrial scale.

In some embodiments, the boron containing reagent is a borate ester, for example, a metaborate ester.

Borate esters are easy to handle and result in a homogenous reaction solution in a $C_{1-9}$-alkanes. It is also proposed that borate esters promote less decomposition of the radical initiator compared with other boron compounds.

In some embodiments the amount of boron containing reagent is from 1 to 10 mol % with respect to the amount of alkane.

Boron containing reagents can reduce the reaction rate of the oxidation process by heterolytic cleavage of the hydroperoxide intermediates formed. By controlling the amount of the boron containing reagent, the reaction rate can be maintained and useful conversion levels can be achieved.

In some embodiments, the free radical initiator is a peroxide, for example, a dialkyl peroxide such as di-tert-butyl peroxide (DTBP).

It is proposed that a peroxide initiator has a longer half-life under the reaction conditions than other initiators and provides a more sustained supply of chain initiating radicals.

In some embodiments the drying means is a drying agent. It may be that the drying agent is a molecular sieve, preferably the molecular sieve is a 3 Å molecular sieve and even more preferably the molecular sieve is a 3 Å molecular sieve with 4 to 8 mesh.

It is proposed that the molecular sieve maintains good drying properties under the reaction conditions. In this way, the molecular sieve can readily remove water from the reaction, reducing unwanted hydrolysis of the intermediate borate ester and improving selectivity to the desired alcohol.

In some embodiments, the mixture may be contacted with oxygen using an oxygen containing atmosphere, preferably the oxygen containing atmosphere is provided by a mixture of oxygen and nitrogen gases. The mixture of oxygen and nitrogen gases may contain from about 1 to 10 vol % oxygen.

In this way the oxygen concentration in the reaction medium promotes efficient oxidation and provides a safe reaction medium (i.e. higher oxygen concentration may result in an explosive mixture being formed during the reaction).

In some embodiments, the mixture is at a temperature of 130° C. to 150° C.

In some embodiments, the mixture is at a temperature of 130° C. to 150° C. for 0.5 to 8 hours, for example from 0.5 to 4 hours, preferably from 1 to 2 hours.

Prolonged reaction times result in lower selectivity. Without wishing to be bound by theory it is proposed that over longer reaction times the over-oxidation to ketone or acid products occurs resulting in lower selectivity.

In some embodiments the method further comprises a hydrolysis step wherein a borate ester produced during the oxidation is treated with water thereby to give an alcohol, such as a sec-alcohol.

It is proposed that water will substitute the alcohol groups bound to the boron by nucleophilic attack on the boron. In this way the desired alcohol product can be recovered from the reaction.

In some embodiments the method further comprises a conversion step wherein the alcohol product produced during the oxidation is converted to an olefin, an ester, an ether or a higher molecular weight product. For example, the alcohol product may be converted to an olefin by dehydration, an ester by reacting with an acid, an ether by partial dehydration, or to a higher molecular weight product by condensation.

In some embodiments the method further comprises a conversion step wherein the borate ester produced during the oxidation reaction is converted directly to an olefin by thermal decomposition at high temperature, for example, at 300° C. or above. That is the conversion step is carried out without the need to first recover the alcohol from the borate ester, for example, by hydrolysis.

In some cases, after the oxidation reaction is deemed complete unreacted alkane is recovered and can be re-used, for example, in a subsequent oxidation reaction. Recovery of the unreacted alkane can be achieved, for example, by fractionation.

In another aspect of the invention there is provided a composition for the oxidation of $C_{1-9}$-alkanes. The composition comprises a $C_{1-9}$-alkane in the liquid phase, a boron containing reagent, a free radical initiator and a drying means, for example a drying agent.

These and other aspects and embodiments of the invention are described in further detail below.

SUMMARY OF THE FIGURES

In FIG. 5(b) plotted lines through filled shapes show the total yield of products and plotted lines through un-filled shapes show the sec-pentanol selectivity at different times for the reaction. [T: 130° C., P: 2.5 MPa (25 bar), $y_{O_2,in}$: 0.1].

In FIG. 16(a) plotted lines through filled shapes show the total yield of products and plotted lines through un-filled shapes show the sec-pentanol selectivity at different times for the reaction. [T: 150° C., P: 3 MPa (i.e. 30 bar), $y_{O_2,in}$: 0.05, $C_{DTBP}$: 10 vol %, 15 g sieves].

DETAILED DESCRIPTION OF THE INVENTION

Figure 1:
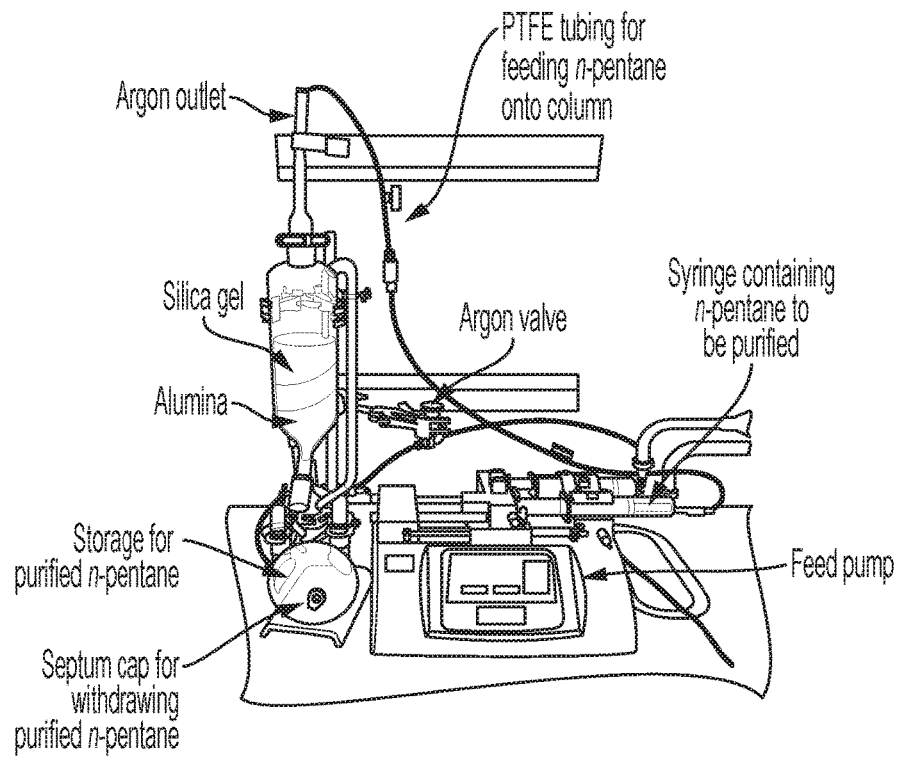
FIG. 1 shows the apparatus for purification of commercial n-pentane.

The present invention provides a method for the oxidation of $C_{1-9}$-alkanes, the method comprising providing a mixture of a $C_{1-9}$-alkane in the liquid phase, a boron containing reagent, a free radical initiator and a drying means. The mixture is provided at a temperature from 130° C. to 180° C. and in the presence of oxygen. In some embodiments, the mixture is at a pressure from 2 to 5 MPa (i.e. 20 to 50 bar).

The method of the invention provides an industrially viable process with good selectivity for alcohol products.

Such processes are not known in the art despite similar processes for longer chain alkanes being known for many years and the long existing desire to adapt such processes to shorter chain alkanes.

Alkanes

The methods of the invention relate to the oxidation of $C_{1-9}$-alkanes. The alkanes are linear alkanes (for example, n-pentane) or branched linear alkanes (for example, iso-hexane). Preferably the alkanes are linear alkanes.

In some embodiments the alkane may be a $C_{3-9}$-alkane, it may be a $C_{3-6}$-alkane, it may be a $C_{4-9}$-alkane, it may be a $C_{4-8}$-alkane, it may be a $C_{4-7}$-alkane, it may be a $C_{4-6}$-alkane, it may be a $C_{5-9}$-alkane, it may be a $C_{5-8}$-alkane, it may be a $C_{5-7}$-alkane, it may be a $C_{5-6}$-alkane, and preferably it may be $C_5$-alkane.

In some embodiments the alkane is $C_5$-alkane, i.e. pentane. Preferably the pentane is n-pentane.

The alkane may be treated prior to reaction to remove undesirable impurities, for example, impurities that are present in the commercial source of the alkane. Undesirable impurities include aromatic compounds, water, olefins, or oxygen-containing compounds. One or more of the impurities are effectively removed after the treatment. An impurity may be present in less than 5 ppm in the alkane. The level of impurity may be measured using gas chromatography or NMR.

The treatment may include passing the alkane through a packed bed of adsorbents. The adsorbents may be silica gel, alumina or a mixture of both. The adsorbents adsorb the impurities and so remove them from the alkane as the alkane passes through the bed.

The undesirable impurities are reduced or are not present during the oxidation reaction. In this way any adverse effect on the oxidation reaction caused by the impurity is reduced.

Boron Containing Reagent

The present invention provides an oxidation method using a boron containing reagent. The boron containing reagent may be a boric acid (e.g. orthoboric acid or metaboric acid), a borate ester (e.g. an orthoborate ester or a metaborate ester) or boric oxide. Preferably the boron containing reagent is a borate ester or boric acid, even more preferably the boron containing reagent is a borate ester.

Borate esters are derived from boric acids (e.g. orthoboric acid or metaboric acid) or from boric oxide in which one or more substituents are attached to the oxygen atoms.

A number of structurally different borate esters exist as shown below.

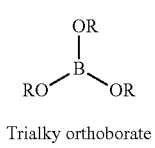

Trialky orthoborate

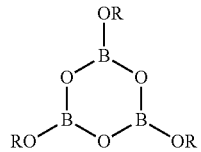

Trialkyl metaborate

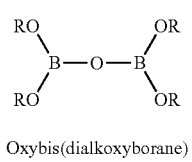

Oxybis(dialkoxyborane)

The R groups, or substituents, may be selected from alkyl groups, aryl groups, benzyl groups, alkyl-carbonyls, alkyl-amides, alkyl-amines or alkyl-ethers. Preferably the R groups are alkyl groups.

In some cases, the R groups on the borate ester may be the same as the alkyl group corresponding to the alkane to be oxidized. The borate ester will transesterify the alcohol produced during the oxidation as discussed above.

In this way when the alcohol is recovered from the reaction, for example by hydrolysis of the borate ester, only one type of alcohol is released from the boron species. This offers simplification of the process since there is no need for downstream separation of two different alcohols as in the case when the starting borate ester reagent has a different R group to the alkane.

In the present invention, the borate ester may be an orthoborate ester (e.g. a trialkyl ortho borate ester such as tri-iso-propyl borate), a metaborate ester (e.g. a trialkyl metaborate such as sec-butyl metaborate) or an oxybisdi-alkoxyborane.

Preferably the borate ester is a metaborate ester, in particular sec-butyl metaborate.

Borate esters are easy to handle and result in a homogenous reaction solution in a $C_{1-9}$-alkanes. It is also proposed that the borate esters are more effective for directing the decomposition of hydroperoxides to alcohols. For example, it may be that the borate esters promote less decomposition of the radical initiator compared with other boron compounds due to the modified Lewis acidity of the borate esters.

In some embodiments the amount of boron containing reagent is from 1 to 10 mol %, for example, from 5 to 10 mol %, and preferably from 3 to 7 mol % with respect to the amount of $C_{1-9}$-alkane.

In some embodiments the amount of boron containing reagent is less than or equal to 10 mol %, for example, less than or equal to 9 mol %, less than or equal to 8 mol %, less than or equal to 7 mol %, less than or equal to 6 mol % or less than or equal to 5 mol % with respect to the amount of $C_{1-9}$-alkane.

In some embodiments the amount of boron containing reagent is greater than or equal to 1 mol %, for example, greater than or equal to 2 mol %, greater than or equal to 3 mol %, greater than or equal to 4 mol %, greater than or equal to 5 mol % or greater than or equal to 6 mol % with respect to the amount of $C_{1-9}$-alkane.

The upper and lower limits for the boron containing reagent amounts may be combined to provide a range in any combination of the amounts provided above.

The heterolytic decomposition of the hydroperoxide intermediate means that radicals are not formed to propagate the chain reaction. In this way, it is proposed that the heterolytic decomposition promoted by the boron containing reagent inhibits the reaction rate. By controlling the amount of the boron compound, the reaction rate can be maintained and useful conversion levels can be achieved.

The boron containing reagents used in the present invention are Lewis acids. A Lewis acid is a chemical species that contains an empty orbital which is capable of accepting an electron pair from a Lewis base to form a Lewis adduct. Lewis acid strength can be measured using the Gutmann-Beckett method which is an experimental procedure using triethylphosphine oxide ($Et_3PO$, TEPO) as a probe molecule. The systems are evaluated by $^{31}P$ NMR spectroscopy. The $^{31}P$ chemical shift (δ) of $Et_3PO$ is sensitive to chemical environment but can usually be found between +40 and +100 ppm. The O atom in $Et_3PO$ is a Lewis base, and its interaction with Lewis acid sites causes deshielding of the adjacent P atom. Gutmann described an Acceptor Number (AN) scale for solvent Lewis acidity with two reference points relating to the $^{31}P$ NMR chemical shift of $Et_3PO$ in the weakly Lewis acidic solvent hexane (δ=41.0 ppm, AN 0) and in the strongly Lewis acidic solvent $SbCl_5$ (δ=86.1 ppm, AN 100). Acceptor numbers can be calculated from AN=2.21×($δ_{sample}$−41.0) and higher AN values indicate greater Lewis acidity.

For boron containing compounds the chemical shifts are typically obtained at room temperatures in neat samples of the borate ester or solution in THF. For discussion of procedure for the Gutmann-Beckett method for boron containing compounds see: Beckett et. al. 2001; Beckett et al. 1996; and Sivaev et al. 2014.

In some embodiments the boron containing reagent has an acceptor number (AN) of from 10 to 100, for example, from 20 to 90, and preferably from 50 to 85 as measured using the Gutmann-Beckett method as described above.

In some embodiments the boron containing reagent has an acceptor number (AN) of less than or equal to 100, for example, less than or equal to 95, less than or equal to 90, less than or equal to 85, less than or equal to 80, or less than or equal to 30 as measured using the Gutmann-Beckett method as described above.

In some embodiments the boron containing reagent has an acceptor number (AN) of greater than or equal to 10, for example, greater than or equal to 20, greater than or equal to 30, greater than or equal to 50, greater than or equal to 60 or greater than or equal to 65 as measured using the Gutmann-Beckett method as described above.

The upper and lower limits for the acceptor number (AN) of the boron containing species may be combined to provide a range in any combination of the amounts provided above.

Some typically acceptor numbers (AN) for known boron compounds are shown in table 2 for reference.

TABLE 2

Lewis acidity of selected oxyboron compounds.

| Boron compound | Acceptor number (AN) |
| --- | --- |
| $(C_2H_5O)_3B$ | 17.1 |
| $(n-C_3H_7O)_3B$ | 20.3 |
| $(i-C_3H_7O)_3B$ | 21.6 |
| $(n-C_4H_9O)_3B$ | 11.8 |
| $(C_2H_5OBO)_3$ | 80.1 |
| $(n-C_3H_7OBO)_3$ | 79.1 |
| $(i-C_3H_7OBO)_3$ | 73.5 |
| $(n-C_4H_9OBO)_3$ | 77.9 |

Source: (Sivaev et al. 2014; Beckett et al. 2001).

It is proposed that higher Lewis acidity of the boron containing reagent improves the selectivity of the process. As discussed above, it is proposed that boron containing reagent improves alcohol selectivity because they induce the heterolytic decomposition of the intermediate hydroperoxide formed during oxidation. That is, it is proposed that the boron containing reagent largely direct the process through a non-radical pathway that favors alcohol formation. This means that the intermediate acid, ROOH, does not decompose to a large extent by the homolytic pathway that favors ketone formation.

Free Radical Initiator

The method of the invention uses a free radical initiator.

It is proposed that the free radical initiator promotes oxidation of the alkanes by carrying on or initiating the radical chain reaction which produces the sec-alcohol product. In this way, it is proposed that the free radical initiator compensates for the inhibition of the reaction by the boron containing reagent which can promote heterolytic decomposition of the hydroperoxide intermediate.

The free radical initiator is a compound that produces a radical when treated with heat or light.

The free radical initiator may be selected from any known free radical initiator, for example, the free radical initiator may be azobisisobutyronitrile (AIBN), a peroxide (for example, di-tert-butyl peroxide) or a hydroperoxide (for example, tert-butyl hydroperoxide (TBHP)).

In some cases the free radical initiator is selected from azobisisobutyronitrile (AIBN), di-tert-butyl peroxide, tert-butyl hydroperoxide, tert-butyl perbenzoate, benzoyl peroxide or acetyl eroxide. In some cases, free radical initiator is selected from azobisisobutyronitrile (AIBN), di-tert-butyl peroxide or tert-butyl hydroperoxide, Preferably, the free radical initiator is a peroxide, for example, a dialkyl peroxide such as di-tert-butyl peroxide (DTBP).

The boron containing reagent can promote heterolytic decomposition of the hydroperoxy linkage. Peroxides do not contain a hydroperoxy group and are not decomposed in the presence of a boron containing reagent. In this way, a peroxide initiator has a longer half-life under the reaction conditions and provides a more sustained supply of chain initiating radicals.

In some embodiments the amount of free radical initiator is from 0.5 to 15 vol %, for example, from 1 to 15 vol %, from 5 to 15 vol %, from 7 to 15 vol %, from 8 to 15 vol %, from 1 to 13 vol %, from 5 to 13 vol %, from 7 to 13 vol %, from 8 to 13 vol %, from 1 to 12 vol %, from 5 to 12 vol %, from 7 to 12 vol %, from 8 to 12 vol %, from 1 to 11 vol %, from 5 to 11 vol %, from 7 to 11 vol %, or from 8 to 11 vol %.

In some embodiments the amount of free radical initiator is less than or equal to 15 vol %, for example, less than or equal to 13 vol %, less than or equal to 12 vol %, or less than or equal to 11 vol %.

In some embodiments the amount of free radical initiator is greater than or equal 0.5 vol %, for example, greater than or equal to 1 vol %, greater than or equal to 5 vol %, greater than or equal to 7 vol %, or greater than or equal to 8 vol %.

In some embodiments the amount of free radical initiator is from 0.5 to 10 mol %, for example, from 5 to 10 mol %, and preferably from 3 to 7 mol % with respect to the amount of $C_{1-9}$-alkane.

In some embodiments the amount of free radical initiator is less than or equal to 10 mol %, for example, less than or equal to 9 mol %, less than or equal to 8 mol %, less than or equal to 7 mol %, less than or equal to 6 mol % or less than or equal to 5 mol % with respect to the amount of $C_{1-9}$-alkane.

In some embodiments the amount of free radical initiator is greater than or equal to 0.5 mol %, for example, greater than or equal to 1 mol %, greater than or equal to 2 mol %, greater than or equal to 3 mol %, greater than or equal to 4 mol %, greater than or equal to 5 mol % or greater than or equal to 6 mol % with respect to the amount of $C_{1-9}$-alkane.

The upper and lower limits for the free radical initiator amounts may be combined to provide a range in any combination of the amounts provided above.

Drying Means

The method of the present invention uses a drying means to remove water from the reaction mixture during the reaction.

In some embodiments of the present invention the drying means is a drying agent. The drying agent sequesters water from the reaction medium by trapping water, for example by forming an intermolecular bond or bonds such as a hydrogen bond between the water and the drying agent. This means that the water is not freely available to react with other components in the mixture.

In this way, the drying agent prevents decomposition of the borate ester produced during the reaction by water. This means that the boron containing reagent can effectively trap the sec-alcohol product (as the borate ester) and prevent over-oxidation.

In some embodiments the drying agent is non-acidic. For example, the drying agent is not Lewis acidic or Bronsted acidic.

The drying agent sequesters water from the reaction medium. For example, the amount of free water (i.e. water that is not sequestered by the drying agent) in the reaction mixture may be less than 100 ppm. In some cases it may be less than 50 ppm, it may be less than 20 ppm or preferably it may be less than 10 ppm. It may be that the amount of free water (i.e. water that is not sequestered by the drying agent) in the reaction mixture may be greater than 1 ppm.

In some embodiments the drying agent is a molecular sieve, preferably the molecular sieve is a 3 Å molecular sieve and even more preferably the molecular sieve is a 3 Å molecular sieve with 4 to 8 mesh or 8 to 12 mesh.

It is proposed that the molecular sieve maintains good drying properties under the reaction conditions. In this way, the molecular sieve can readily remove water from the reaction, reducing unwanted hydrolysis of the intermediate borate ester and improving selectivity to the desired alcohol. It is also proposed that the molecular sieve has a high selectivity for water and so remove less of the product alcohols. In this way, the alcohol product can be recovered in higher yields more efficiently.

The molecular sieve may be activated by drying in an oven prior to use, for example by drying at 250° C. to 260° C. prior to use.

A molecular sieve is a synthetic or naturally occurring zeolite materials or metal aluminosilicates, with the general chemical formula: $xK_2O.(1-x)Na_2O. Al_2O_3.2SiO_2.nH_2O$, where x is the fraction of potassium ions in the type 3 Å for example, x may be from 0.05 to 0.95, x may be from 0.4 to 0.8, x may be from 0.5 to 0.7.

In some embodiments of the invention the drying means is a semi-permeable membrane, for example, a hydrophilic pervaporation membrane.

The semi-permeable membrane contains pores which allows water to pass through the membrane. The pores reduce the amount of or prevent larger compounds from passing through (e.g. due to size of the pores) and so water can be effectively removed from the reaction mixture. In the case of a hydrophilic pervaporation membrane the passage of water through the membrane may be driven by a pressure differential across the membrane.

The semi-permeable membrane may be located within the reactor. Alternatively the semi-permeable membrane may be located downstream of the reactor and, if so, the reaction mixture may be re-circulated back to the reactor. The contact of the reaction mixture with the membrane is set to achieve sufficient contact time for removal of the product water from the reaction mixture. This will vary for different membranes and reaction conditions, for example, by taking into account the transmembrane flux specific to the membrane used and the reaction conditions.

Semi-permeable membranes such as hydrophilic pervaporation membranes do not require periodic regeneration to maintain their drying properties. In this way, the use of a semi-permeable membrane provides the advantage of continuous operation.

The pervaporation membrane may be an inorganic pervaporation membrane (e.g. a zeolite-based membrane prepared by sol-gel synthesis or a silica-based membrane), an organic pervaporation membrane (e.g. a composite membrane containing polyvinyl alcohol active layer or a perfluoropolymer active layer), an inorganic-organic nano-composite pervaporation membrane (e.g., a membrane in which an active polymer layer includes inorganic nanoparticles) or an organic-inorganic hybrid pervaporation membrane (e.g., a hybrid inorganic-organic polymer).

Preferably the pervaporation membrane is an organic pervaporation membrane, an inorganic-organic nano-composite pervaporation membrane or an organic-inorganic hybrid pervaporation membrane. More preferably the membrane is an organic-inorganic hybrid pervaporation membrane such as a hybrid inorganic-organic polymer.

It is proposed that organic-inorganic hybrid pervaporation membranes such as hybrid inorganic-organic polymers offer a higher temperature stability compared to, for example, organic membranes.

In some embodiments drying of the reaction mixture is carried out using a drying agent, for example a molecular sieve, and a semi-permeable membrane, for example a pervaporation membrane. That is the drying means is a combination of a drying agent and a semi-permeable membrane.

Oxygen Atmosphere

In the method of the present invention, the reaction is performed in the presence of an oxygen containing atmosphere. The contact with oxygen provides an oxidizing environment to oxidize the alkane.

In some embodiments, the mixture may be contacted with oxygen using an oxygen containing atmosphere, preferably the oxygen containing atmosphere is provided by a mixture of oxygen and nitrogen gases.

The mixture of oxygen and nitrogen gases may contain from about 1 to 10 vol % oxygen, for example, the mixture may contain from 1 to 9 vol % oxygen, from 1 to 8 vol % oxygen, from 1 to 7 vol % oxygen, from 1 to 6 vol % oxygen, from 1 to 5 vol % oxygen, from 2 to 10 vol % oxygen, from 2 to 9 vol % oxygen, from 2 to 8 vol % oxygen, from 2 to 7 vol % oxygen, from 2 to 6 vol % oxygen, from 2 to 5 vol % oxygen, from 3 to 10 vol % oxygen, from 3 to 9 vol % oxygen, from 3 to 8 vol % oxygen, from 3 to 7 vol % oxygen, from 3 to 6 vol % oxygen, from 3 to 5 vol % oxygen, from 4 to 10 vol % oxygen, from 4 to 9 vol % oxygen, from 4 to 8 vol % oxygen, from 4 to 7 vol % oxygen, from 4 to 6 vol % oxygen, from 4 to 5 vol % oxygen, from 5 to 10 vol % oxygen, from 5 to 9 vol % oxygen, from 5 to 8 vol % oxygen, from 5 to 7 vol % oxygen or from 5 to 6 vol % oxygen.

In some preferred cases the mixture of oxygen and nitrogen gases may contain from 3 to 7 vol % oxygen, from 4 to 6 vol % oxygen or from 5 to 10 vol % oxygen. The remaining volume is made up of nitrogen.

In this way the oxygen concentration in the reaction medium promotes efficient oxidation and provides a safe reaction medium (i.e. higher oxygen concentration may result in an explosive mixture being formed during the reaction).

Reaction Conditions

In the method of the present invention, the reaction mixture is held at 130° C. to 180° C. The temperature of the reaction is selected to achieve a good rate of reaction.

In some embodiments the reaction may be held at from 130 to 170° C., from 130 to 160° C., from 130 to 150° C., from 140 to 180° C., from 140 to 160° C. or from 140 to 150° C. Preferably, the reaction is held at from 130 to 150° C.

The pressure of the reaction needs to be sufficient to maintain the alkane substantially in liquid form during the reaction at the temperatures employed.

For smaller alkanes a higher pressure will be required to maintain the alkane in liquid form compared to a larger alkane at the same temperature. For example, at a temperature of 130 to 150° C., a pressure of from 2 to 3 MPa (20 to 30 bar) is preferred for $C_5$-alkanes such as n-pentane.

In some embodiments the method of the present invention is carried out at from 2 to 5 MPa (i.e. 20 to 50 bar). Preferably the reaction is carried out at from 2 to 3 MPa (i.e. 20 to 30 bar), for example, the reaction may be carried out at from 2 to 2.5 MPa (i.e. 20 to 25 bar) or from 2.5 to 3 MPa (i.e. 25 to 30 bar). The reaction may be carried out, for example, at around 3 MPa (i.e. 30 bar) or around 2 MPa (i.e. 20 bar).

In some embodiments, the method of the present invention is carried out for a time from 0.5 to 8 hours, for example from 0.5 to 4 hours, preferably from 1 to 2 hours.

Prolonged reaction times have been found to result in lower selectivity. Without wishing to be bound by theory it is proposed that over longer reaction times the over-oxidation to ketone or acid products occurs resulting in lower selectivity.

The end point of the reaction may be determined by a number of factors depending on the desired outcome. For example, shorter reaction times (e.g. 0.5 to 2 hours) may be desirable to give greater selectivity or longer reaction times (e.g. 2 to 8 hours) may be desirable to give greater conversion. The end point may be determined by routine measurement of the reaction mixture at various time points and by selecting the time point which provides the desirable product amounts.

Additional Steps

The method of present invention may comprise one or more of the following additional steps.

In some embodiments the method further comprises a hydrolysis step wherein a borate ester produced during the oxidation is treated with water thereby to give an alcohol, such as a sec-alcohol.

It is proposed that water will substitute the alcohol groups bound to the boron by nucleophilic attack on the boron. In this way the desired alcohol product can be recovered from the reaction.

In some embodiments the method further comprises a conversion step wherein the alcohol produced during the oxidation is converted to an olefin, an ester, an ether or a higher molecular weight product. The alcohol may be recovered from the borate esters by any suitable method, for example, by hydrolysis (as discussed above).

For example, the alcohol product may be converted to an olefin by dehydration, an ester by reacting with an acid, an ether by partial dehydration, or to a higher molecular weight product by condensation.

In some embodiments the method further comprises a conversion step wherein the borate ester produced during the oxidation reaction is converted directly to an olefin by thermal decomposition at high temperature, for example, at 300° C. or above (see Lappert, M. F. 1956).

In this case, the conversion step is carried out without the need to recover the alcohol from the borate ester by hydrolysis.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"And/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL DETAILS AND RESULTS

Experimental work on the liquid-phase oxidation of n-pentane with molecular oxygen in the presence of a free radical initiator and boron compounds in a semi-batch reactor is presented.

The influence of operating parameters, such as temperature, total pressure, oxygen content in the feed gas as well as radical initiator and boron concentrations, on the rate of oxidation, yield of oxidation products and selectivity to sec-pentanols have been evaluated.

Materials

Anhydrous n-pentane (99.9%), di-tert-butyl peroxide, DTBP (Luperox®, 98%), 1,4-difluorobenzene (>99%), boric oxide (99.98% trace metal basis), molecular sieves 3 Å (4-8 mesh beads; Honeywell UOP, and Fisher Scientific), silica gel (60 Å pore size, 35-60 mesh particle size) and activated basic alumina (58 Å pore size, ~150 mesh particle size) were sourced from Sigma-Aldrich, UK.

Triisopropyl borate (AcroSeal™, >98%) was purchased from ACROS Organics, Thermo Fisher Scientific, UK.

sec-Butyl metaborate, s-BuMB, (>98%) was custom-synthesized and supplied by Tyger Scientific Inc., NJ, USA.

All other chemicals apart from n-pentane were used as received without further purifications.

Prior to oxidation runs, anhydrous n-pentane was further purified to remove trace impurities such as aromatics, which may interfere with the oxidation and subsequent analyses, thus invalidating the results obtained. The received n-pentane was treated by percolating it through a packed column containing silica gel (about 100 g) and activated basic alumina (about 100 g) in a specially built glass apparatus shown in FIG. 1.

The apparatus, which comprises a pressure-equalizing funnel and a 500 mL round-bottom flask, was cleaned, washed with deionized water and dried before assembly. Stopcocks and joints were wrapped with Teflon tapes. Both silica gel and alumina were previously heated to 300° C. in an oven for 12 hours, thereafter cooled to room temperature and stored in a desiccator until use. Pentane purification was started by passing argon at 0.15 MPa (i.e. 1.5 bar) pressure and flow rate of 20 mL (STP) min$^{-1}$ through the apparatus to exclude air.

Activated alumina was transferred into the glass column, which was plugged at the base with a small piece of wool, followed by silica gel at the top. A syringe pump (PHD Ultra, Harvard Apparatus, USA) was then used to pump anhydrous pentane through a 1/16 inch PTFE tubing to the top of the adsorbents at a rate of 5 mL min$^{-1}$ with continuous flow of argon through the set-up. Pentane percolates through the adsorbents, and into the 500 mL reservoir, from which the desired amount for oxidation runs was taken with a syringe through a PTFE septum.

The experimental apparatus used consists of a stainless-steel autoclave fitted with a condenser, which cools and recycles most of the vaporized n-pentane and other volatile compounds in the outlet gas stream.

The limiting oxygen concentration (LOC), which is the maximum safe oxygen level for the required operating temperature and pressure, was estimated and was found to be 10.2 vol % oxygen, with the rest being an inert gas.

Measurements

Identification and quantitative analyses of oxidation products were undertaken on an Agilent 7890B GC integrated with a 5977B MSD and fitted with a CTC PAL autosampler. Gas phase was analyzed on the GC and liquid analyses performed on the MS. The GC was equipped with two thermal conductivity detectors (TCDs), one for light gases such oxygen, carbon monoxide and methane, and the other for heavier molecules such as carbon dioxide and higher hydrocarbons. Helium was used as the carrier gas with a flow rate of 3 mL min$^{-1}$. The GCMS side was equipped with a DB-WAX column (30 m long, 250 m diameter and 0.25 m film thickness) suitable for separating polar compounds.

For gas analysis, the inlet temperature and pressure were set to 250° C. and 82.3 psi, respectively, while the detectors were maintained at 250° C. Oven temperature was held at 35° C. for 3 min then ramped at 10° C. min$^{-1}$ to 90° C. and held for 1.5 min, and finally increased to 190° C. at a rate of 10° C. min$^{-1}$. Analysis time was 20 minutes with a further 3 minutes for post-run at 230° C.

Analyses of the liquid products were performed on the MS by taking 100 µL aliquots and diluting to 1 mL in ethyl acetate. Inlet temperature was 300° C. while the oven was programmed at 80° C. for 1 minute, then ramped at 20° C. min$^{-1}$ to 140° C. and subsequently to 200° C. at 50° C. min$^{-1}$ and held for 1 min. Split ratio was 100:1 and total analysis time was 6.2 minutes.

For experimental runs with boron compounds, both aqueous and organic phases were analyzed, so that the total concentration of oxidation products is given by the sum of the amounts of the product in both phases, as written in Equation 1.

$$C_i = C_{i,aq} + C_{i,org} \quad \text{(Equation 1)}$$

Qualitative analysis of the aqueous phase showed no presence of 1,4-difluorobenzene. Hence, for quantitative analyses of the aqueous samples, an amount of internal standard was added equivalent to that present in the diluted organic phase samples (i.e. 13.947/10=1.395 µL per mL). This was done by preparing a stock solution containing 20 µL 1,4-difluorobenzene in 980 µL ethyl acetate. 69.7 µL of this solution was then pipetted and added to the 100 µL aqueous phase samples, with the balance being ethyl acetate solvent.

The identity of each compound was established using NIST MS library and subsequently confirmed by injecting authenticated analytical standards. Calibration and quantification of the main products were performed on an Agilent Mass Hunter™ quantitative analysis software based on their individual response factor relative to the internal standard. The calibration curves obtained are shown in Appendix B.3.

Due to high volatility of n-pentane, accurate determination of the conversion of the hydrocarbon was very challenging. Thus, analysis of the reactor performance was based on product selectivity and yield, defined in Equations 2 and 3, respectively.

$$S_{s-PeOH} = \frac{\text{mol of } s\text{-pentanol}}{\sum \text{mol of liquid-phase products}} \times 100\% \quad \text{(Equation 2)}$$

$$Y_i = \frac{\text{mol of product } i}{\text{initial mol of } n\text{-pentane}} \times 100\% \quad \text{(Equation 3)}$$

General Method—Apparatus

Figure 2:
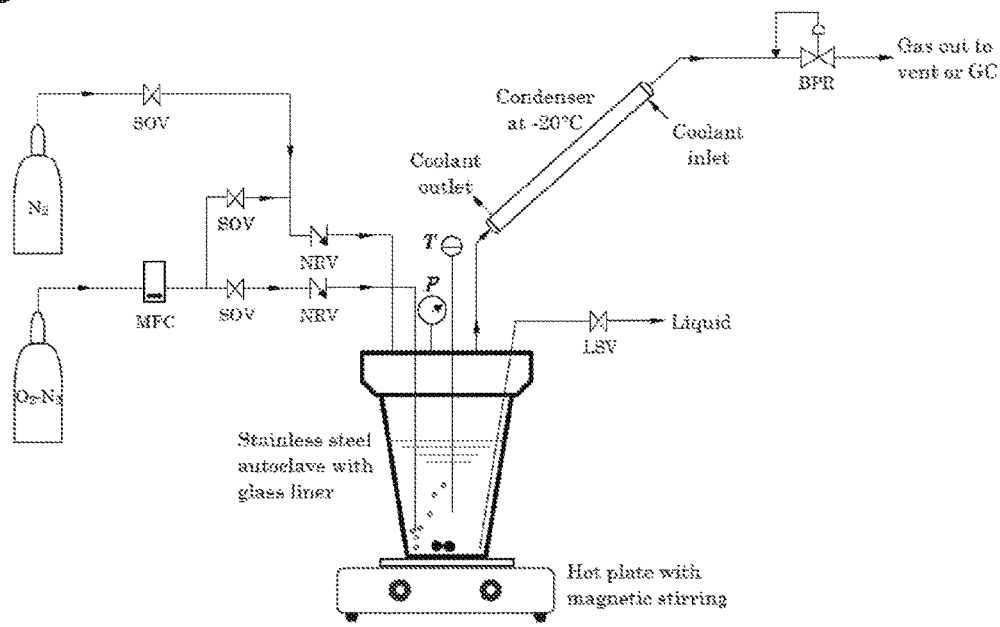
FIG. 2 shows a schematic view of the semi-batch reactor for oxidation of n-pentane for use in an embodiment of the invention. MFC: Mass flow controller; NRV: non-return valve; BPR: back pressure regulator; SOV: shutoff valve; LSV: liquid sampling valve.

The oxidation of n-pentane was carried out in a semi-batch reactor, shown schematically in FIG. 2. The apparatus is batch with respect to liquid and continuous with respect to the gas phase. The reactor set-up consists of a 150 mL stainless steel autoclave (HEL Ltd, UK) rated to 10 MPa (i.e. 100 bar) and 250° C. A glass vessel was placed in the autoclave to prevent leaching of metal ions into the reaction mixture. A Perlast® perfluoroelastomer (FFKM) o-ring between the lid and the base of the autoclave ensured a good seal once the reactor was closed. Heating was provided by placing the autoclave on a hot plate with aluminum inserts to support the vessel and to improve heat transfer. The reactor was also equipped with a pressure gauge, an IKA ETS-D5 temperature probe (IKA-Werke GmbH, Germany) with an accuracy of +0.5° C., a magnetic stirrer and liquid sampling tube for taking samples periodically from the reactor without perturbing the pressure in the system.

The outlet of the autoclave was connected to a 70 cm long stainless-steel condenser, with 1,3-propanediol/water mixture as a coolant circulated by a Thermo Haake DC30/K20 cooling bath. The coolant was maintained at −20° C., and the gas exiting the condenser flowed through an electronic-pneumatic back pressure regulator (BPR), which maintained a stable back pressure inside the reactor. The BPR is an RHPS series dome-loaded pressure regulator with an adjustable pressure range of 0-150 barg connected to an electronic high-pressure regulator assembly consisting of a forward pressure controller and transducer (Proportion-Air Inc, USA). The desired downstream pressure setpoint was achieved by supplying nitrogen at 0.7 MPa (i.e. 7 bar) to the BPR dome and adjusting the voltage command signal on a 0-10 VDC analog potentiometer, which corresponds to 0-90 barg calibrated range. The exit gas from the BPR goes through a three-way valve, which led to the vent or the gas chromatography (GC) for analysis. The line was heated to prevent condensation of vapors such as acetaldehyde.

Gas supply to the reactor consists of nitrogen, which was used to displace air from the setup before the start of experimental runs and to clear the lines of vapors at the end of experiments. A second gas cylinder contains the oxidizing gas, containing between 5 and 10 vol % oxygen in nitrogen. The gas flow rate was controlled by a calibrated Sierra SmartTrak 100 mass flow controller (MFC; Sierra Instruments) with an accuracy of +1%. To rapidly pressurize the reactor the highest flow rate on the MFC was used and the gas entered the reactor through the inlet at the top of the autoclave to minimize splashing of liquid. At the start of oxidation the gas was adjusted to the desired flow rate and directed through the sparger to ensure uniform dispersion of gas bubbles into the liquid phase and promote gas-liquid mass transfer. The experimental rig was placed in a safety cabinet constructed with aluminum frames and 6 mm thick polycarbonate sheets and fitted with a fume extractor for the reactor off-gas.

General Method—Oxidation Procedure

Three different types of experiments were performed: thermal oxidation of n-pentane, initiated oxidation of n-pentane with DTBP, and oxidation of n-pentane with DTBP initiator and boron compounds.

Most of the oxidation experiments in the presence of boron species were conducted with s-BuMB with some experiments undertaken with triisopropyl borate (TiPrB) and boric oxide.

A description of the procedure for oxidation in the presence of s-BuMB is given below, but the steps followed are same for other experiments.

In a typical run, freshly activated molecular sieves, which had been heated in an oven at 260° C. for 12 hours and thereafter cooled to room temperature in a desiccator, were weighed into the reactor. The autoclave was covered with the lid and air excluded from the apparatus with a flow of nitrogen. Thereafter, 1,4-difluorobenzene internal standard, DTBP radical initiator, purified n-pentane and s-BuMB were charged into the reactor. n-Pentane (70 mL) was used in all experiments, and the concentration of internal standard was kept the same as 13.947 µL per mL of starting materials. The amount of s-BuMB used was varied between 1.5 and 6.8 mol % relative to n-pentane. Density of s-BuMB was taken as 0.985 g mL$^{-1}$ at 20° C. (Lappert 1958). All liquid materials were measured using Hamilton gas-tight syringes with an accuracy of +1%.

The desired back pressure was set by applying the appropriate voltage on the potentiometer (i.e. 3.33 V for 3 MPa (30 bar)). The vent gas valve was shut and the reactor was pressurized with nitrogen (BOC Gases, UK) using the maximum flow rate on the MFC. The flow of nitrogen was directed to the top of the liquid in the reactor to minimize splashing of liquid in the space between the glass vessel and the inside of the autoclave. Heating was turned on and when the reactor reached the desired temperature, flow through the MFC was switched to the oxidizing gas and directed through the sparger placed inside the liquid mixture. Flow rate of the oxidizing gas was maintained at 50 mL min-1 and the content of the reactor was stirred at 500 rpm to ensure good mixing of gas and liquid phases. Duration of each experiment was 8 hours. Samples of the liquid oxidation product were withdrawn periodically, while at the same time the exiting gas phase from the reactor was sent to the GC for analysis of gaseous products. During sampling, the liquid sampling tube was first purged by taking and discarding ~250 µL of liquid, followed by ~500 µL of liquid for analysis.

To recover alcohols, the liquid samples were treated with 1 mL of deionized water at 50° C. to hydrolyze borate esters. The mixture was shaken thoroughly and left to stand for 20 minutes to ensure complete hydrolysis. Analyses of aliquots of the resulting aqueous and organic layers were undertaken on a GCMS. The procedure described above was followed for the oxidation of n-pentane in the presence of TiPrB and boric oxide.

During thermal and DTBP-initiated oxidations, no boron compound is present in the reaction medium, and thus the liquid samples were analyzed directly without hydrolysis.

Boron Compounds

Figure 3A:
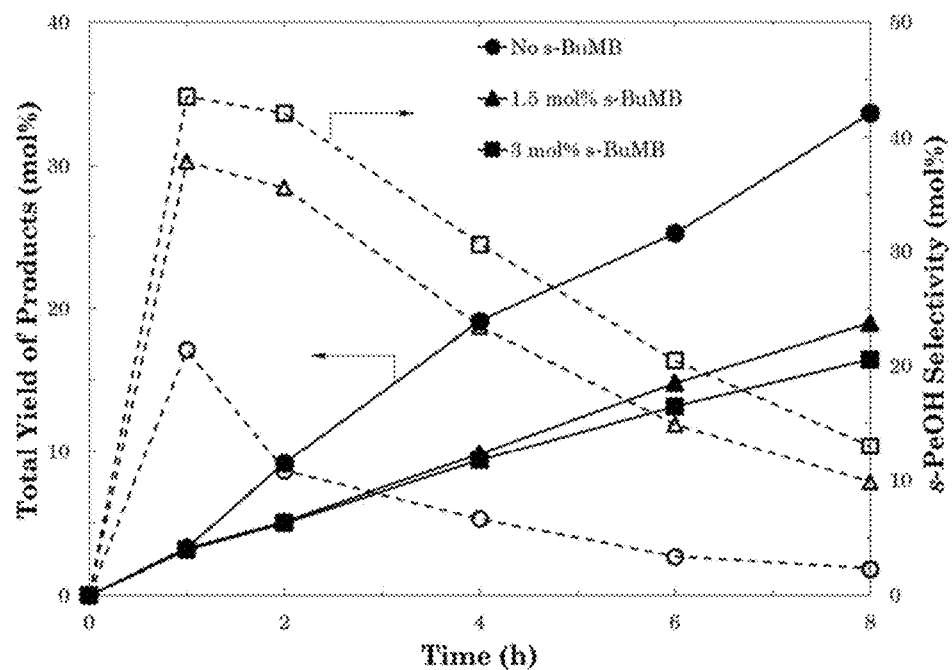
FIGS. 3(a) and 3(b) are graphs of selectivity vs time showing the effect of sec-butyl metaborate on the oxidation of n-pentane. Plotted lines through filled shapes show the total yield of products and plotted lines through un-filled shapes show the sec-pentanol selectivity at different times for the reaction. [(a) T: 150° C., P: 3 MPa (30 bar), $y_{O_2,in}$: 0.1, $C_{DTBP}$: 1 vol %, 10 g mol. sieves. (b) T: 130° C., P: 2.5 MPa (25 bar), $y_{O_2,in}$: 0.1, 12 g sieves].

The influence of boron on the oxidation of n-pentane was investigated with different concentrations of s-BuMB as shown in FIG. 3. First, the initiated oxidation experiment with 10% oxygen in the feed gas presented in FIG. 4 was repeated twice, with 1.5 mol % and 3 mol % s-BuMB, and the results obtained are shown in FIG. 3(*a*).

In the early stages of the reaction up to about 1 hour, the initiated oxidations of n-pentane in the presence of the metaborate ester proceeded almost as efficiently as with DTBP only.

It is proposed that the reaction retains its fundamental free-radical chain characteristic even in the presence of boron (Sakaguchi et al. 1972; Woods and Brotherton 1970). Beyond the initial period, however, oxidation with the boron compound progressively gives lower overall yield of the oxygenated products, with 18.9% after 8 hours for the run with 1.5 mol % s-BuMB initiated by DTBP compared to 33.2% for the oxidation with DTBP only. Doubling the concentration of s-BuMB further reduced the total product yield to 16.5% after 8 h.

The presence of the boron compound improves sec-pentanol selectivity, the optimum values of which were attained after 2 hours of reaction. With 1.5 mol % s-BuMB, the maximum selectivity was 37.9% at 3.24% yield compared to 21.4% at 3.31% yield for oxidation without DTBP alone. Doubling the concentration of boron to 3 mol % further improved sec-pentanol selectivity, giving a maximum of 43.5% at 3.16% yield after 2 hours.

FIG. 3(*b*) shows the results of oxidation runs at 130° C. with 3 mol % sec-butyl metaborate. The run with 8 vol % DTBP and no boron was presented earlier in FIG. 5(*b*), where the optimum sec-pentanol selectivity was found to be 22.6% after 2 hours with a corresponding total product yield of 3.46%. In comparison, when this experiment was repeated with 3 mol % s-BuMB added to the reaction medium, FIG. 3(*b*) shows that the rate of oxidation was inhibited, leading to lower yield of the oxygenated products compared to the run without boron. This confirms the inhibiting role of boron on the oxidation process. However, selectivity to sec-pentanols is significantly improved due to the presence of the alkyl metaborate in the reaction medium.

When the concentration of DTBP initiator was increased from 8 to 10 vol % while maintaining the same concentration of the metaborate, FIG. 3(*b*) shows that the rate of oxidation of n-pentane increased to give product yields similar to that achieved with the oxidation without boron specie.

However, there is a consequent reduction in sec-pentanol selectivity compared to the run with 8 vol % DTBP and same amount of metaborate ester. This observation clearly indicates that the higher level of initiator in the reaction medium helped to increase the concentration of chain-initiating radicals, giving higher conversion of n-pentane, and thus yield of oxygenated products.

Furthermore, these results show the feasibility of achieving much improved alcohol selectivity in the presence of boron under conditions that give the same conversion as the oxidation without boron. It is possible to achieve improved selectivity without the typical trade-off in conversion, thus maximizing yield.

The influence of the concentration of sec-butyl metaborate on the oxidation of n-pentane was also investigated with 5 mol % oxygen in the oxidizing gas.

Figure 6:
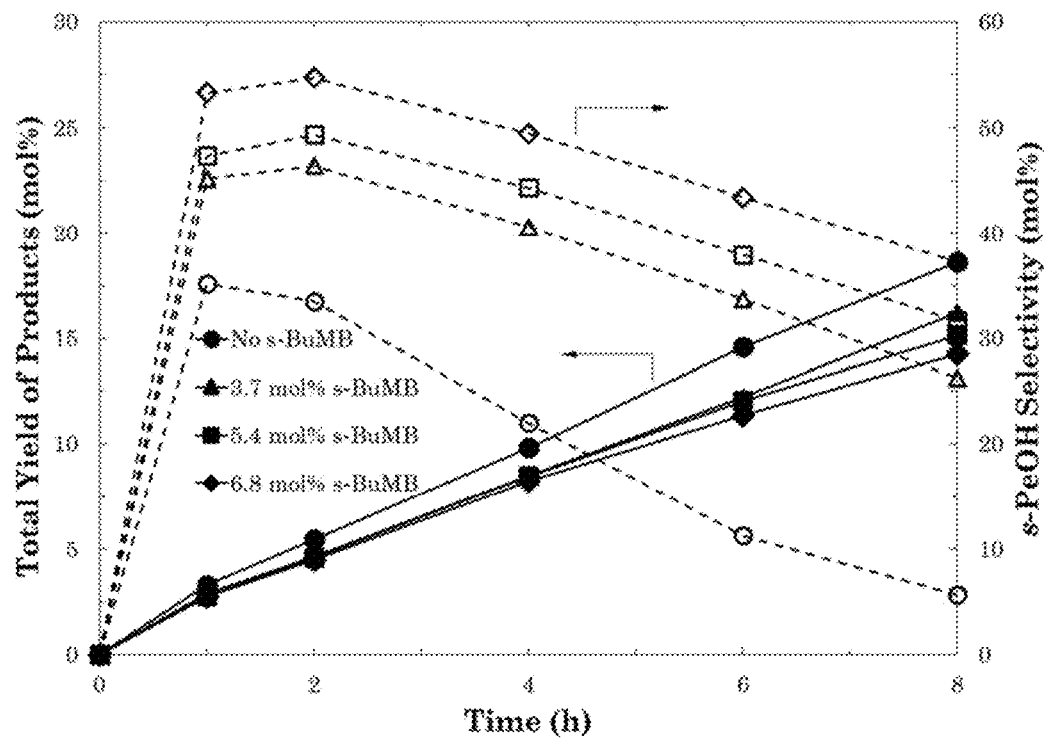
FIG. 6 is a graph of selectivity vs time showing the effect of s-BuMB on initiated oxidation of n-pentane. Plotted lines through filled shapes show the total yield of products and plotted lines through un-filled shapes show the sec-pentanol selectivity at different times for the reaction. [T: 150° C., P: 3 MPa (30 bar), $y_{O_2,in}$: 0.05, $C_{DTBP}$: 10 vol %, 15 g sieves].
Figure 7:
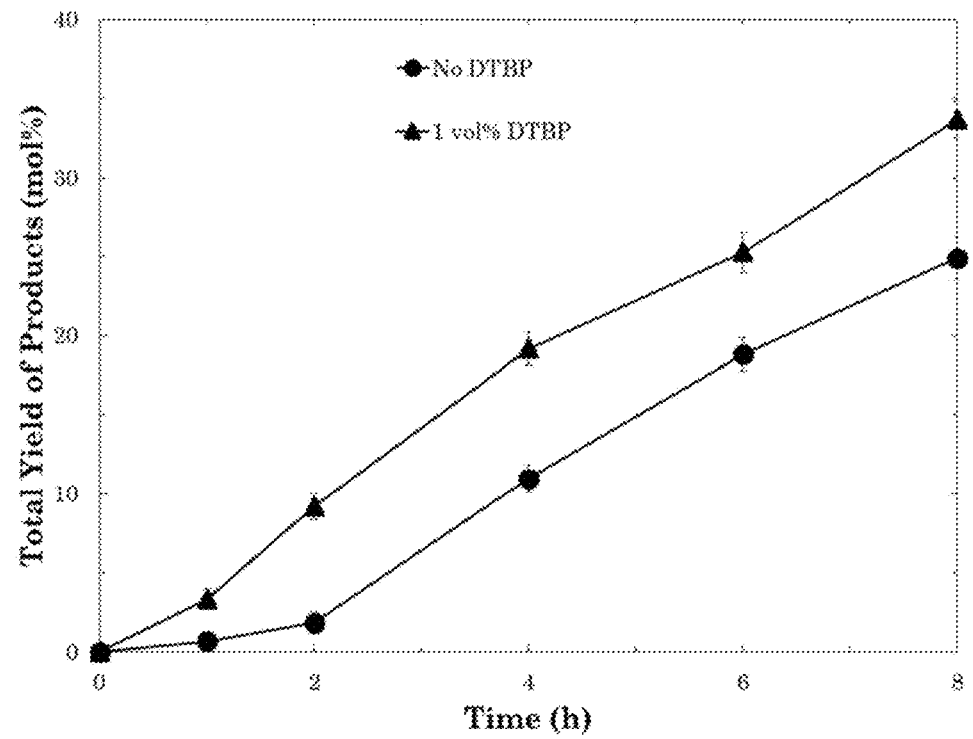
FIG. 7 is a graph of selectivity vs time showing the influence of radical initiator on the initial rate of oxidation [T: 150° C., P: 3 MPa (30 bar), $y_{O_2,in}$: 0.1]. Error bars show repeatability of the experiments.

FIG. 6 shows the overall product yields and selectivity to sec-pentanols obtained during oxidation runs at 150° C. with 10 vol % DTBP initiator. Similar to the trends seen in FIGS. 3(*a*) and 3(*b*), the reactions with and without s-BuMB proceed at fairly similar rates in the early stages of the oxidation but thereafter the product yields with s-BuMB became progressively lower compared to initiated oxidation without boron.

sec-Pentanol selectivity is markedly enhanced by the presence of the boron species, and increases with higher concentration of s-BuMB. Selectivity increases at first, reaching a maximum after 2 hours, and thereafter declines with reaction time due to consecutive oxidation to side products.

The discrepancies between the yield of products with and without s-BuMB in FIGS. 3(*a*) and 3(*b*) and 5(*a*) and 5(*b*) can be attributed to the inhibition of oxidation by the presence of boron, which becomes more pronounced with higher amount of s-BuMB. This effect may be due to the fact that boron lowers the concentration of free radicals in the reaction medium as a result of the heterolytic decomposition of the intermediate sec-pentyl hydroperoxides dominating over the normal radical-producing homolytic cleavage (Wolf and Barnes 1969).

Furthermore, inhibition is more evident in FIG. 3(*a*) than in FIG. 3(*b*) and FIG. 6, which may be due to the higher amount of DTBP used in the latter runs, thus ensuring a more sustained supply of chain propagating radicals in the system. With an increase in the amount of boron, the rate of oxidation decreases as a result of further reduction in the concentration of radicals.

In addition, the improvement in alcohol selectivity observed during the experiments with s-BuMB, discussed above, may be due to the boron compound favoring the decomposition of sec-pentyl hydroperoxides into sec-pentanols, followed by protection of the alcohols in the form of sec-pentyl borates to minimize their over-oxidation.

In other words, the presence of the metaborate ester limits the concentration of sec-pentoxy radicals formed by homolytic fragmentation of the hydroperoxide, and consequently the yields of ketones and acids were lower during oxidation in the presence of the boron Lewis acid.

Table 3 summarizes the optimum selectivity and the corresponding product yield and ROH/R'O ratio after 2 hours of oxidation based on the data presented in FIG. 6.

The results confirm that while the rate of oxidation is fairly the same in the early stages with and without boron, the presence of the metaborate ester alters the product distribution, directing the oxidation towards increased alcohol production.

TABLE 3

Optimum selectivity and yield for oxidation with s-BuMB. [Based on experimental data at 2 h and reaction conditions shown in FIG. 6].
Oxidation with DTBP and s-BuMB

|  | DTBP only | 3.7 mol % s-BuMB | 5.4 mol % s-BuMB | 6.8 mol % s-BuMB |
|---|---|---|---|---|
| s-PeOH selectivity (%) | 33.5 | 46.4 | 49.4 | 54.7 |
| Overall product yield (%) | 5.45 | 4.65 | 4.59 | 4.48 |
| s-PeOH/PeO ratio | 1.06 | 1.93 | 2.17 | 2.56 |

Temperature

The influence of temperature, in the range of 130 to 150° C., on the rate of oxidation and product distribution was studied with and without boron. In the absence of boron compounds, the effect of temperature on the oxidation process was presented and examined in FIGS. 4, 5(*a*), 5(*b*), and 7.

Figure 8:
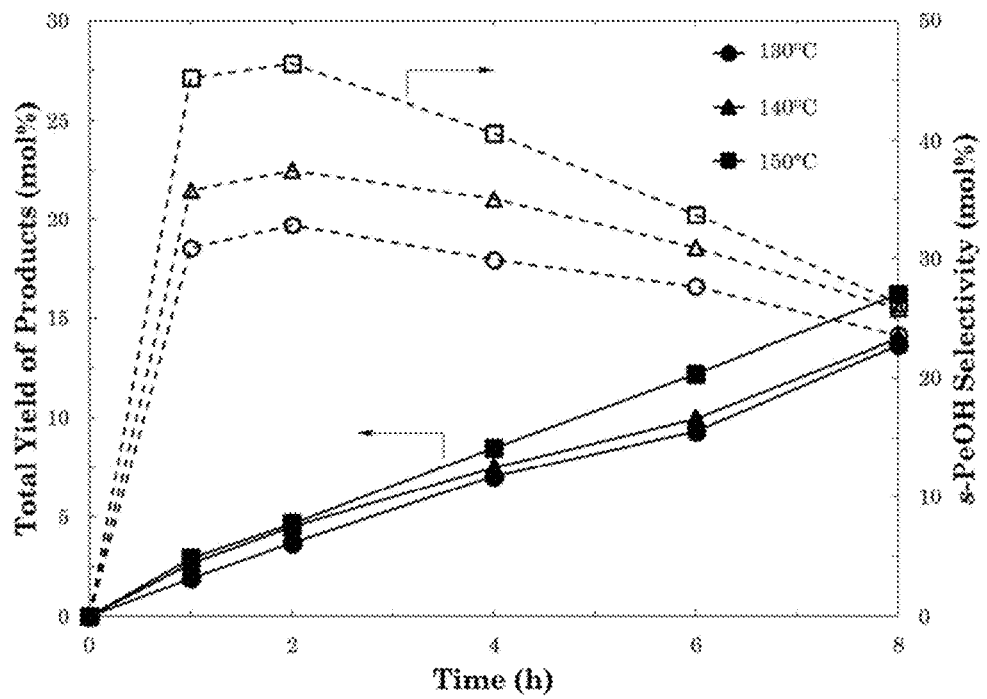
FIG. 8 is a graph of selectivity vs time showing the dependence of yield and selectivity on reaction temperature. Plotted lines through filled shapes show the total yield of products and plotted lines through un-filled shapes show the sec-pentanol selectivity at different times for the reaction. [P: 3 MPa (30 bar), $y_{O_2,in}$: 0.05, $C_{s-BuMB}$: 3.7 mol %, $C_{DTBP}$: 10 vol %, 15 g sieves].

For the oxidation of n-pentane in the presence of boron species at different temperatures, the kinetic curves are presented in FIG. 8.

The results show that the rate n-pentane oxidation increased with temperature as indicated by the higher yield of products. As temperature increases, the rate of thermal homolysis of the radical initiator also increases, leading to higher conversion of the hydrocarbon.

Selectivity to sec-pentanols also improved significantly with the reaction temperature, which may be attributed to two effects. First, higher temperature may be responsible for increasing the rate of heterolytic decomposition of the boron-hydroperoxide intermediate complex to favor sec-pentanols. Second, as temperature increases the equilibrium of transesterification between sec-pentanols and s-BuMB is shifted towards the right to give higher yield of sec-pentyl borate esters, thus sec-pentanols upon hydrolysis.

Figure 4:
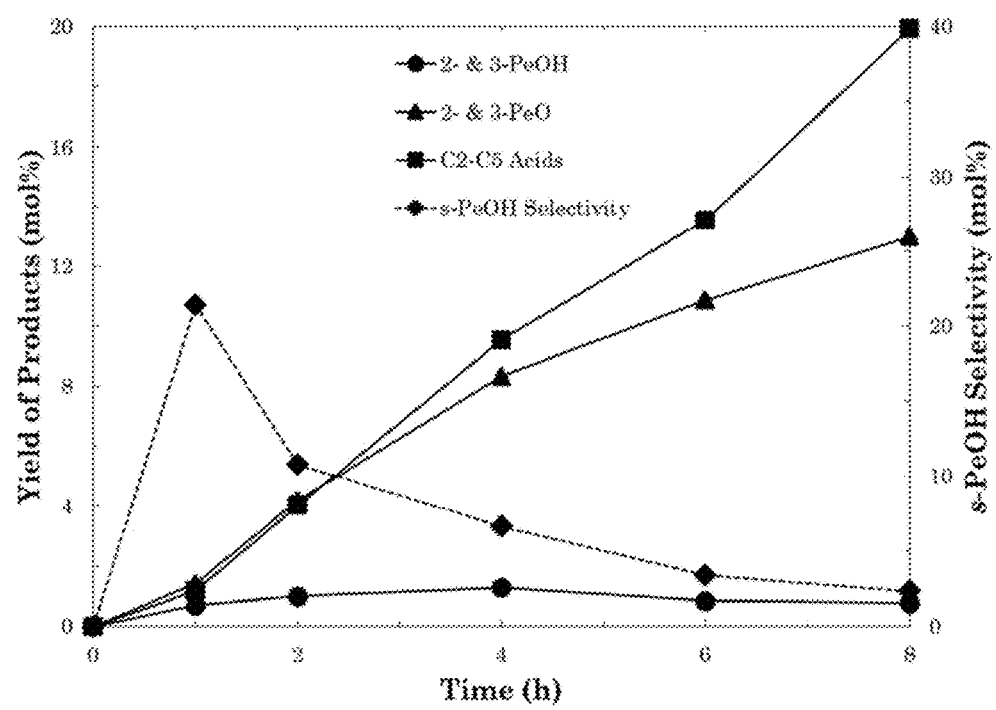
FIG. 4 is a graph of selectivity vs time showing the yield profiles for the initiated oxidation of n-pentane [T: 150° C., P: 3 MPa (30 bar), $y_{O_2,in}$: 0.1, $C_{DTBP}$: 1 vol %].
Figure 5A:
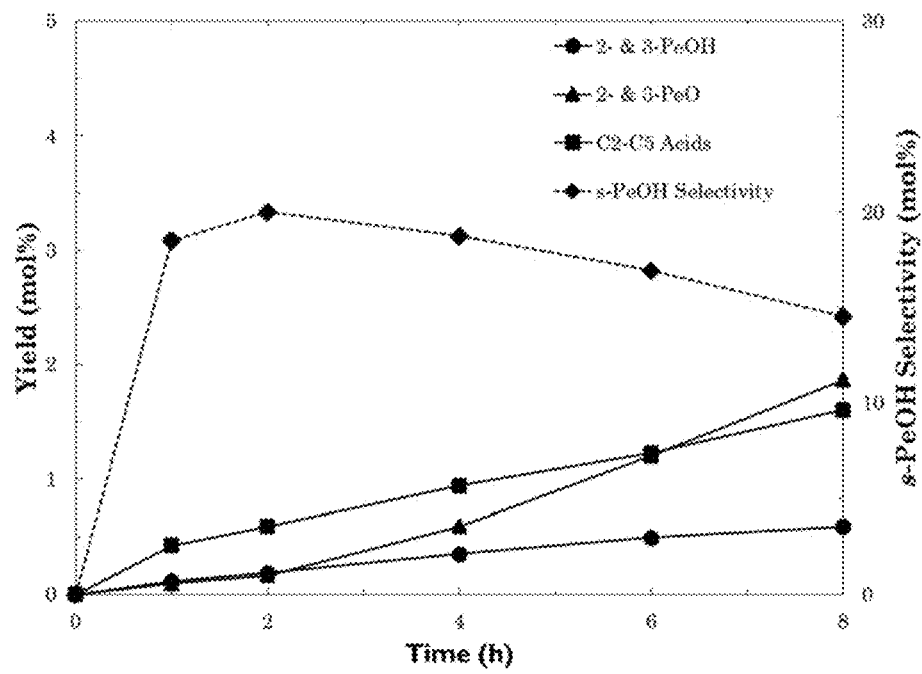
FIGS. 5(a) and 5(b) are graphs of selectivity vs time showing the effect of DTBP concentration on the oxidation without boron. (a) Kinetic curve for oxidation with 1 vol % DTBP (b) Selectivity and yield profiles.
Figure 5B:
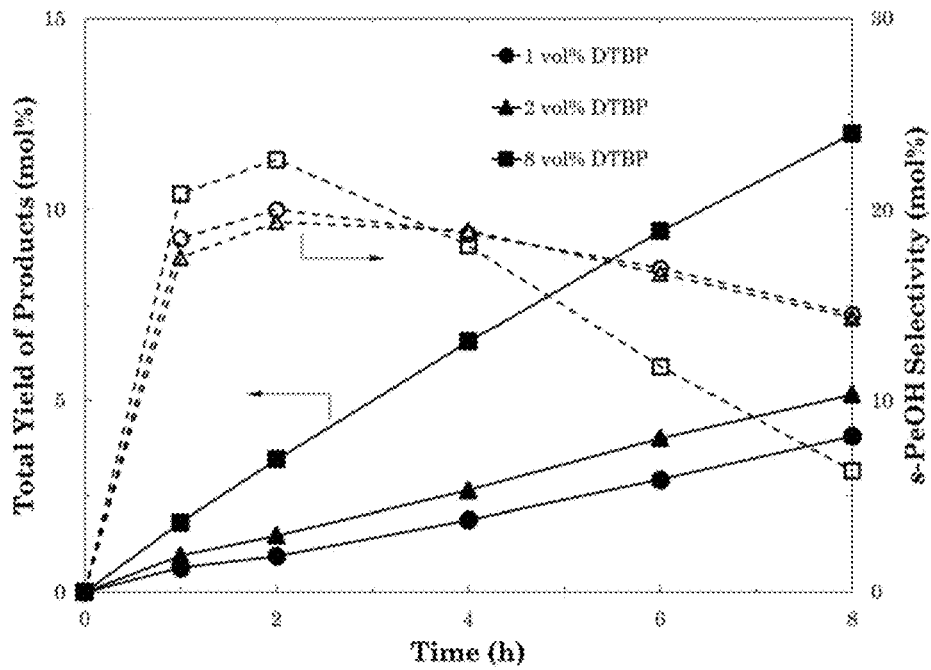

Comparing the oxidation of n-pentane under similar conditions with 1 vol % DTBP in the absence of boron at 130 and 150° C. shown in FIG. 5(*a*) and FIG. 4, respectively, an increase in temperature clearly results in a marked rise in the yield of products, but mostly to pentanones and acids. This is because higher temperatures favor the homolytic cleavage of sec-pentoxy radicals to give acids at the expense of the reaction of the former involving hydrogen abstraction from n-pentane to form sec-pentanols. However, in the presence of boron the situation is reversed, with sec-pentanol selectivity increasing with temperature.

Feed Gas and Pressure

Figure 9:
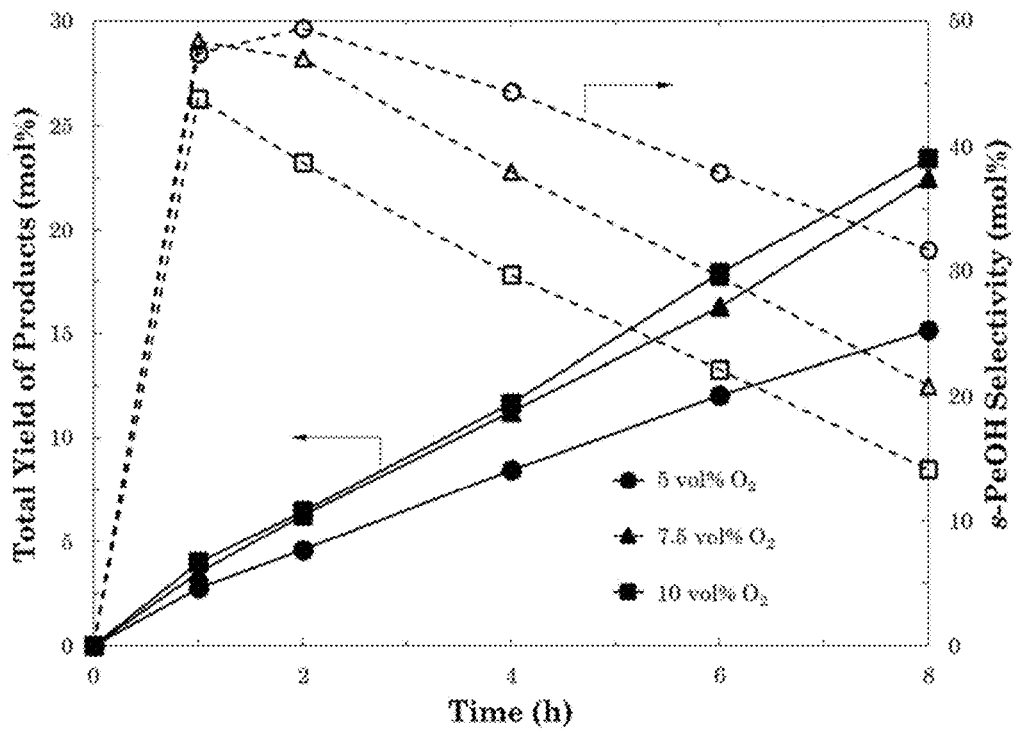
FIG. 9 is a graph of selectivity vs time showing the effect of oxygen concentration on selectivity and yield. Plotted lines through filled shapes show the total yield of products and plotted lines through un-filled shapes show the sec-pentanol selectivity at different times for the reaction. [T: 150° C., P: 3 MPa (30 bar), $C_{s-BuMB}$: 3.7 mol %, $C_{DTBP}$: 10 vol %, 15 g sieves].

The influence of oxygen concentration in the oxidizing gas was investigated with 5 to 10 vol % oxygen in nitrogen. FIG. 9 shows the results of this investigation.

By increasing oxygen content in the feed gas, the initial rates of reaction are increased and the overall yield of products increased with reaction time. However, higher oxygen concentration in the feed gas leads to lower sec-pentanol selectivity.

As the oxygen content increased, the optimum reaction time at which the maximum selectivity was attained shifted slightly; thus for 5 and 10 vol % oxygen in nitrogen, maximum selectivity of 49.1 and 43.8% were attained at around 2 and 1 hour, respectively.

It is proposed that as the partial pressure of oxygen in the gas phase increased, the mass transfer of oxygen into the liquid phase also increased, resulting in an increase in the rate of oxidation and the product yield. Conversely, higher dissolved oxygen concentration increased the rate of consecutive oxidation of sec-pentanols into pentanones and acids as well as total combustion side products such as $CO_2$, thus lowering selectivity. In addition, it may be that the higher rate of oxidation due to increased oxygen concentration could lead to the formation of high levels of moisture, which rapidly saturated the molecular sieves. Free moisture could cause premature hydrolysis of the protected sec-pentanols, thereby exposing them to further oxidative attack into by-products.

Since boron compounds decrease the level of free radicals in the reaction medium, the presence of higher oxygen content ensures more rapid replenishment of the hydroperoxide concentration to maintain the chain process, thus resulting in higher reaction rate with increasing oxygen concentration.

To further investigate the influence of oxygen partial pressure on the reactor performance, oxidation of n-pentane in the presence of s-BuMB was carried out with 5 vol % oxygen in nitrogen at several total pressures in the reactor. The results obtained are shown by the kinetic curves in FIG. 10.

Figure 10:
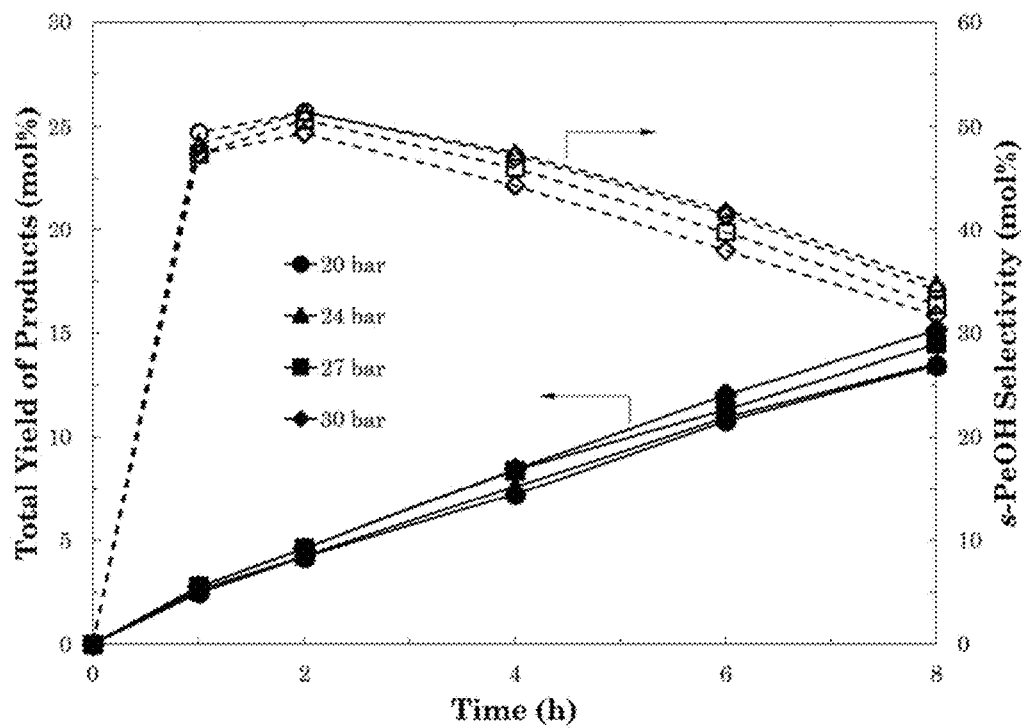
FIG. 10 is a graph of selectivity vs time showing the influence of total pressure on reactor performance. Plotted lines through filled shapes show the total yield of products and plotted lines through un-filled shapes show the sec-pentanol selectivity at different times for the reaction. [T: 150° C., $y_{O_2,in}$: 0.05, $C_{s-BuMB}$: 5.4 mol %, $C_{DTBP}$: 10 vol %, 15 g sieves].

Over the range investigated, the profiles in FIG. 10 show that the effect of total pressure on both the cumulative yield of oxidation products as well as sec-pentanol selectivity was small but not negligible. Conversion, and yield, increased slightly with total pressure, which may be due to the higher availability of dissolved oxygen in the liquid phase.

It is proposed that the increase in total pressure increases the interfacial concentration of oxygen, hence the driving force for mass transfer, which consequently leads to an increase in the total yield of oxygenated products. However, selectivity declines with increased total pressure, due to the higher rate of non-selective over-oxidation of the alcohols.

For reactor pressure of 2 MPa (i.e. 20 bar) after 2 hours of oxidation, overall yield of oxygenated products was 4.18% while the corresponding sec-pentanol selectivity was 51.4%, compared to 4.62% yield and selectivity of 49.1% in the case of 3 MPa (i.e. 30 bar) reactor pressure after the same duration of reaction.

This observation confirms that a small change in oxygen partial pressure can have some effect on the product distribution and selectivity. Apart from the improved selectivity, operating the reactor at 2 MPa (i.e. 20 bar) is advantageous for the process operating cost.

Initiator

Figure 3B:
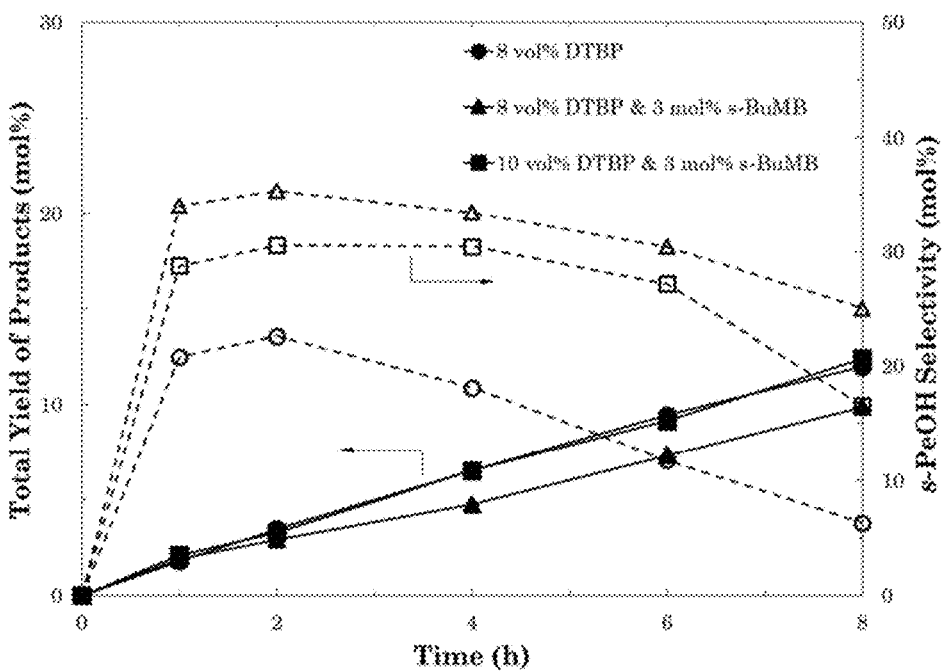

The influence of the concentration of radical initiator at constant level of boron was previously discussed for the oxidation run at 130° C. with an oxidizing gas containing 10% oxygen (see FIG. 3(b)).

Figure 11:
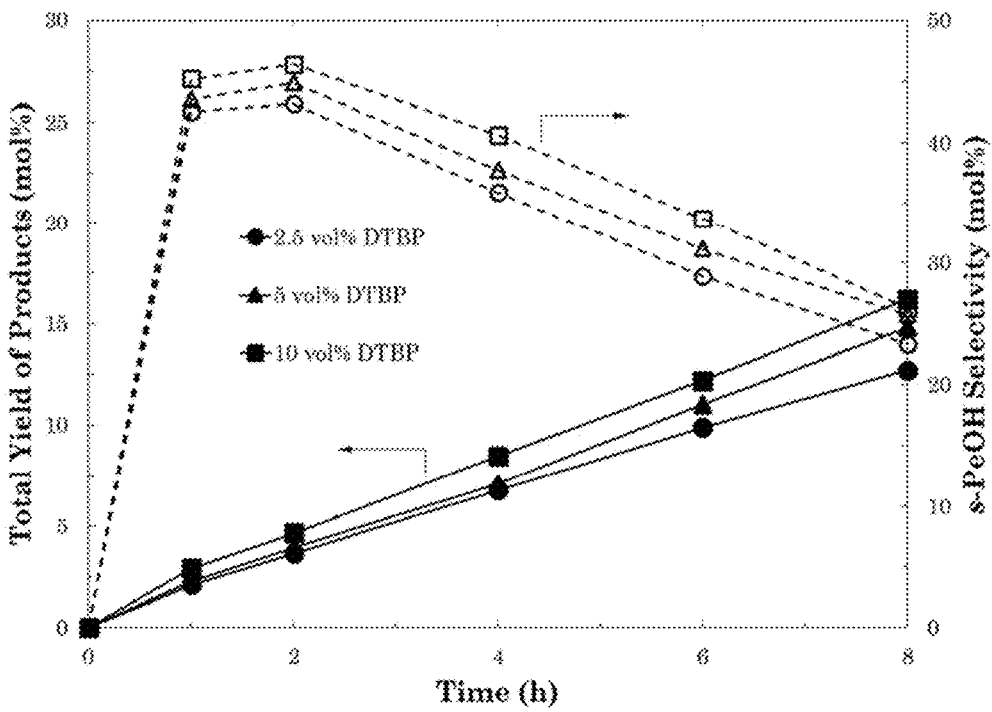
FIG. 11 is a graph of selectivity vs time showing the effect of DTBP concentration on the oxidation with s-BuMB. Plotted lines through filled shapes show the total yield of products and plotted lines through un-filled shapes show the sec-pentanol selectivity at different times for the reaction. [T: 150° C., P: 3 MPa (30 bar), $y_{O_2,in}$: 0.05, $C_{s-BuMB}$: 3.7 mol %, 15 g sieves].

FIG. 11 shows the effect of the initiator under different conditions with 2.5 to 10 vol % DTBP.

The profiles show that both the yield of oxygenated products and the selectivity to sec-pentanols increase with an increase in the concentration of the free radical initiator. The results in FIG. 11 are opposite to those seen in FIG. 3(b), where yield increased but selectivity dropped with higher levels of DTBP.

It is proposed that the differences may be due to the lower oxygen concentration and higher reaction temperature used for the experimental runs presented in FIG. 11, thus favoring the formation of sec-pentanols.

Boron Species

The oxidation of n-pentane was investigated with three different boron compounds of varying Lewis acidity and physical forms: sec-butyl metaborate, triisopropyl borate and boric oxide.

The experimental results obtained when the oxidation was carried with similar molar concentration of the boron species are presented in FIG. 12. These are compared with oxidation without boron.

Figure 12A:
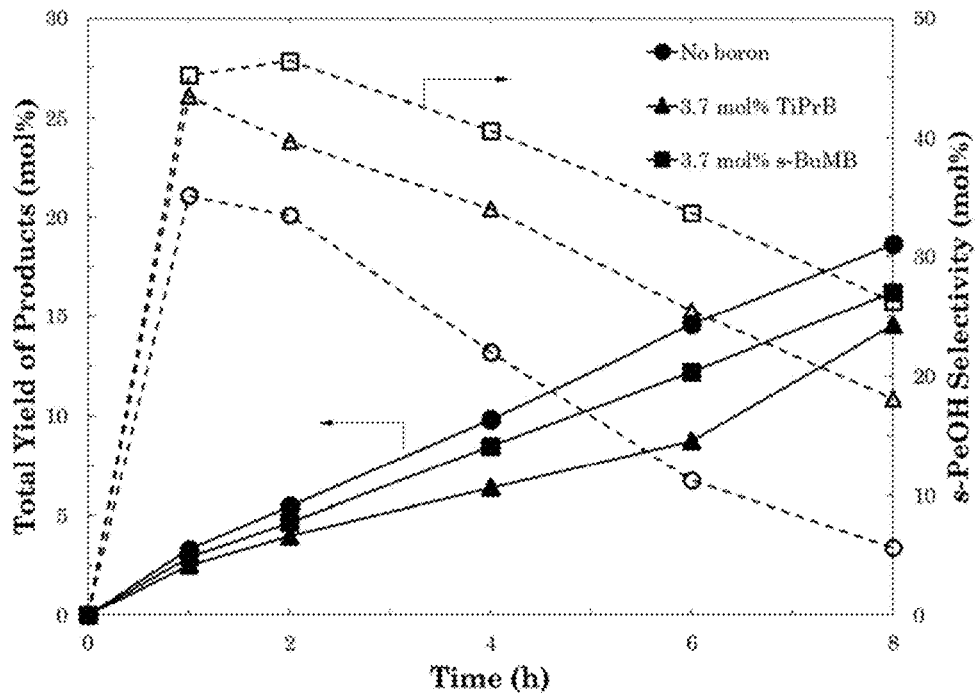
FIGS. 12(a) and 12(b) are graphs of selectivity vs time showing the effect of boron species on product selectivity and yield. Oxidation with: (a) TiPrB and s-BuMB (b) s-BuMB and boric oxide. In both FIGS. 12(a) and 12(b) plotted lines through filled shapes show the total yield of products and plotted lines through un-filled shapes show the sec-pentanol selectivity at different times for the reaction. [T: 150° C., P: 3 MPa (30 bar), $y_{O_2,in}$: 0.05, $C_{DTBP}$: 10 vol %, 15 g sieves].
Figure 12B:
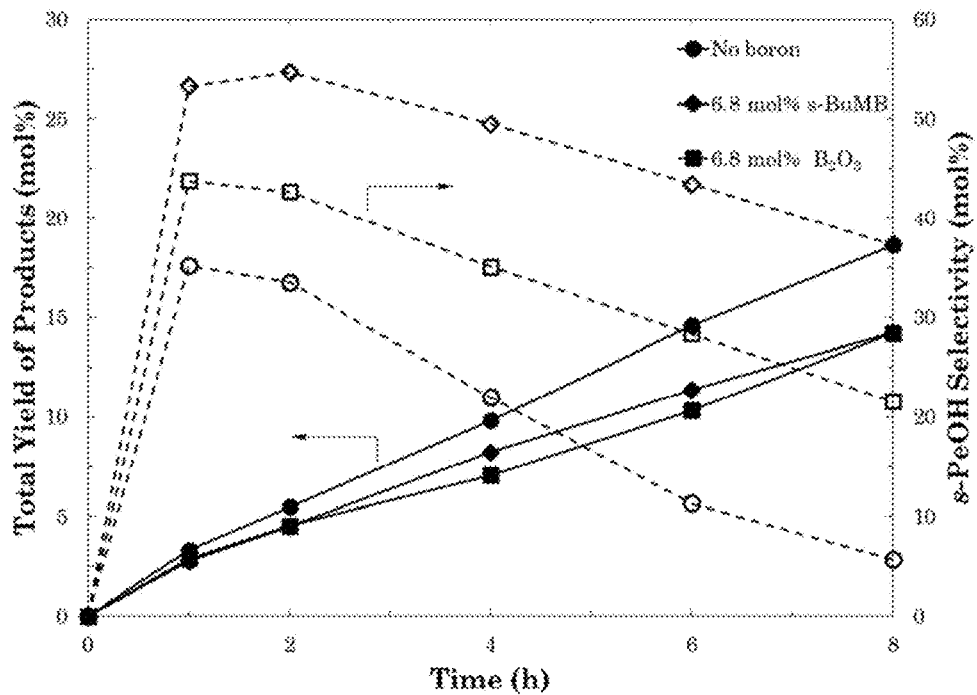
Figure 16A:
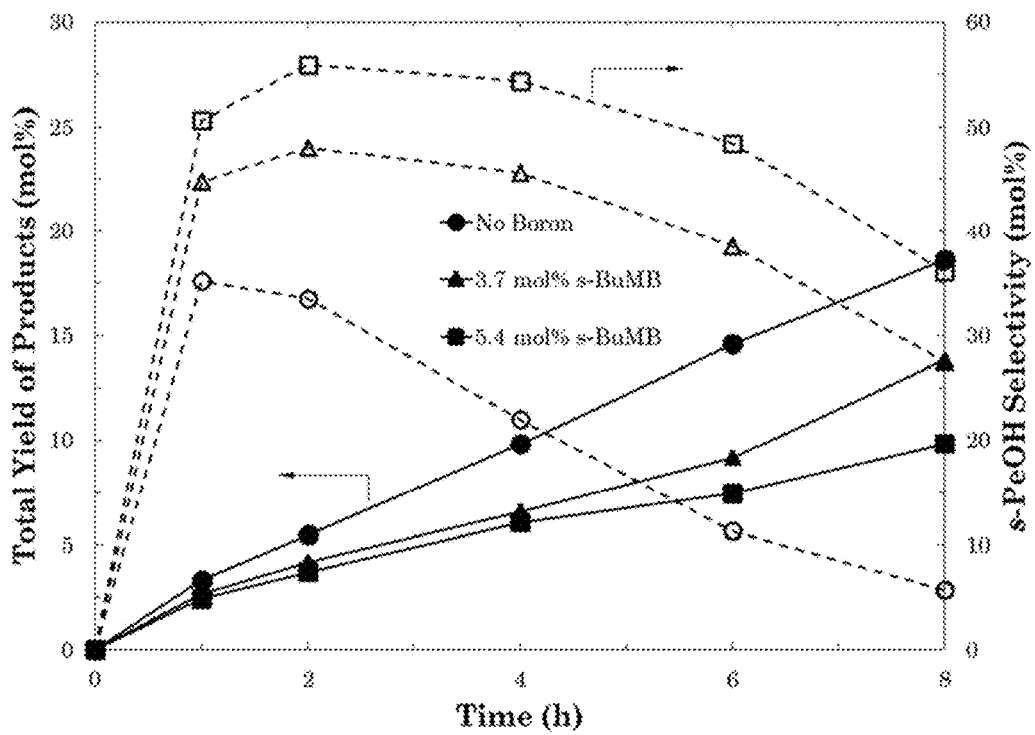
FIGS. 16(a) and 16(b) are graphs of selectivity vs time showing the effect of boron concentration on the oxidation of n-pentane: (a) Yield and alcohol selectivity; (b) Alcohol-to-ketone ratio.

From FIGS. 16(a) and (b), it can be seen that the selectivity and yield profiles for both TiPrB and boric oxide are similar to that of s-BuMB, and all three boron compounds improve alcohol selectivity compared to the oxidation with DTBP only. However, s-BuMB gives higher product yield as well as selectivity to sec-pentanols than TiPrB as shown in FIG. 12(a).

The orthoborate appears to inhibit the oxidation more than the metaborate ester, especially at later stages of the reaction. Furthermore, from FIG. 12(b), the yields of oxidation products are similar for both boron compounds, however, sec-pentanol selectivity is significantly higher for s-BuMB compared to boric oxide.

Based on these findings, it may be suggested that an alkyl metaborate is more effective for directing the oxidation of n-pentane towards the formation sec-pentanols compared to an orthoborate and boric oxide.

The fact that s-BuMB gives better selectivity than the same concentrations of TiPrB and boric oxide effect may be explained by the higher Lewis acidity of alkyl metaborates compared to alkyl orthoborates and boric oxide (Beckett et al. 2001; Sheldon and van Doom 1974; Sakaguchi et al. 1972).

Alcohol to Ketone Ratio

Figure 13:
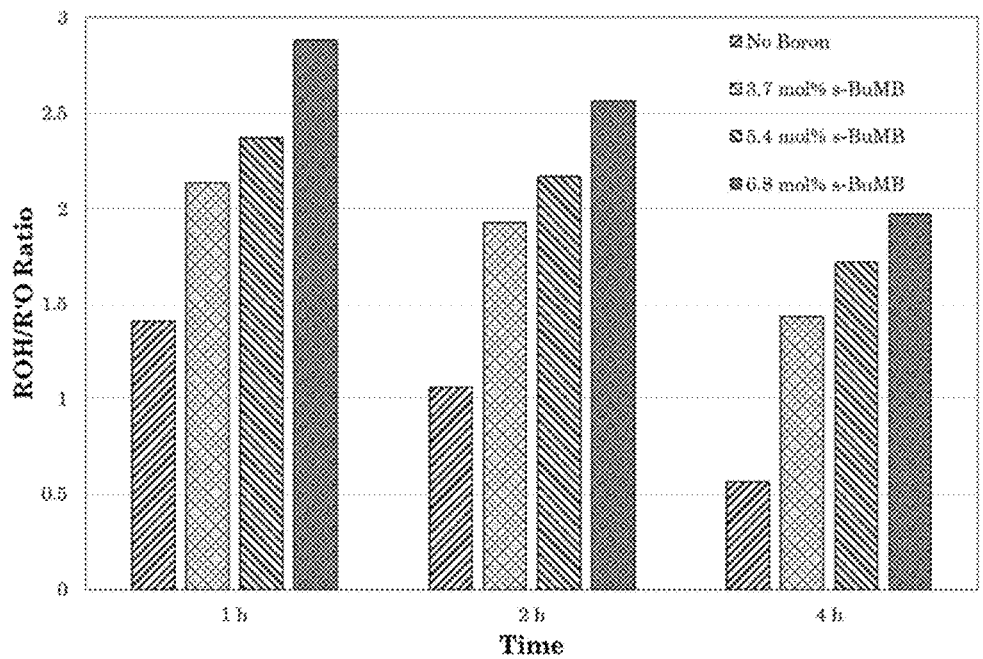
FIG. 13 is a bar chart showing the influence of boron concentration on ROH/R'O ratio. [T: 150° C., P: 3 MPa (30 bar), $y_{O_2,in}$: 0.05, $C_{DTBP}$: 10 vol %, 15 g sieves].

FIG. 13 shows the results for the oxidation of n-pentane without boron as well as with three different concentrations of sec-butyl metaborate. The alcohol to ketone ratio can be used to assess the effectiveness of a boron compound for directing the oxidation towards the formation of alcohols.

In general, the trends follow closely that of sec-pentanol selectivity: maximum alcohol-to-ketone ratio is achieved in the first 1 hour of reaction, regardless of the presence of boron, which thereafter decreases progressively with time.

This observation may be explained by the over-oxidation of the alcohols to pentanones with increasing conversion. Furthermore, oxidation with sec-butyl metaborate clearly gave higher yields of sec-pentanols relative to pentanones compared to oxidation carried out without added boron, and the value increases with increasing boron concentration.

For the oxidation of n-pentane with 3.7 mol % s-BuMB, the optimum alcohol-ketone ratio is 2.14 compared to 1.41 achieved for the oxidation in the absence of boron. The yields of sec-pentanols relative to pentanones increased further to 2.37 and 2.88 for 5.4 mol % and 6.8 mol % sec-butyl metaborate, respectively.

It is proposed that the increase in alcohol production with an increase in the boron concentration is due to an increase in the rate of heterolytic decomposition of sec-pentyl hydroperoxide to form sec-pentanols, as well as the increase in the rate of protective transesterification of the alcohols formed.

Figure 14:
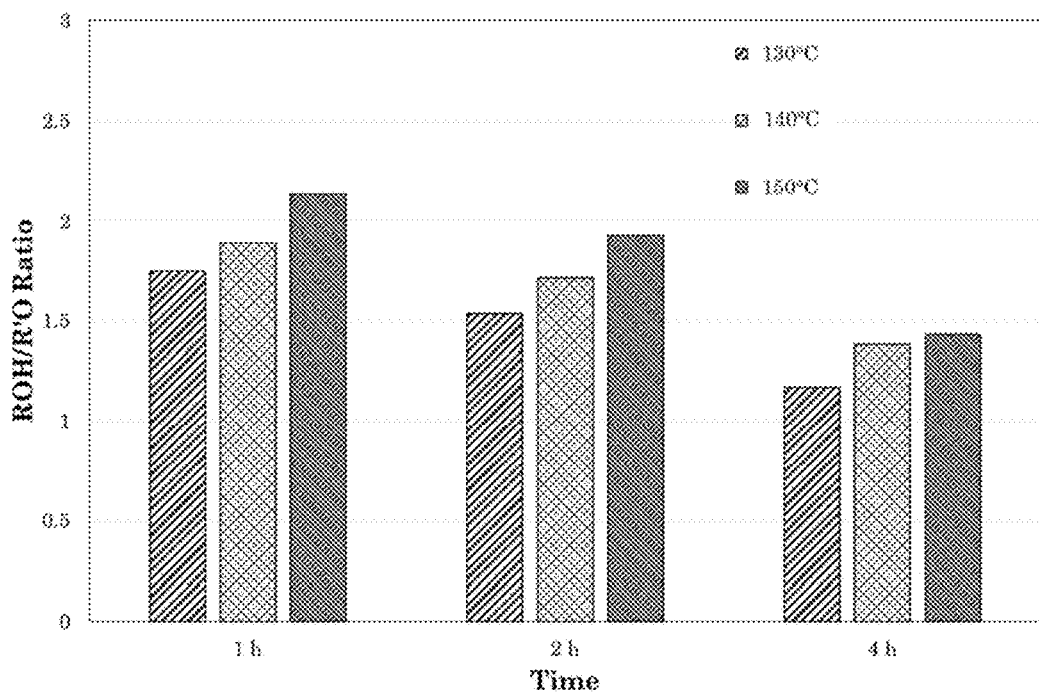
FIG. 14 is a bar chart showing the effect of oxidation temperature on ROH/R'O ratio. [P: 3 MPa (30 bar), $y_{O_2,in}$: 0.05, $C_{s-BuMB}$: 3.7 mol %, $C_{DTBP}$: 10 vol %, 15 g sieves].

FIG. 14 shows the relationship between the alcohol to ketone ratio and the operating temperature. FIG. 14 shows that the yield of sec-pentanols relative to pentanones reached a maximum in 1 hour and subsequently decreased with reaction time.

Comparing the oxidation of n-pentane without boron at 150 and 130° C. shown in FIG. 4 and FIG. 5(a), respectively, the alcohol to ketone ratio decreased with the reaction temperature. In the presence of boron, the ratio increased with temperature as shown in FIG. 14.

It is proposed that the increase in pentanol-to-pentanone ratio with temperature may be due to an increase in the rate of heterolytic decomposition of the boron-hydroperoxide complex selectively into alcohols at the expense of ketones.

Figure 15:
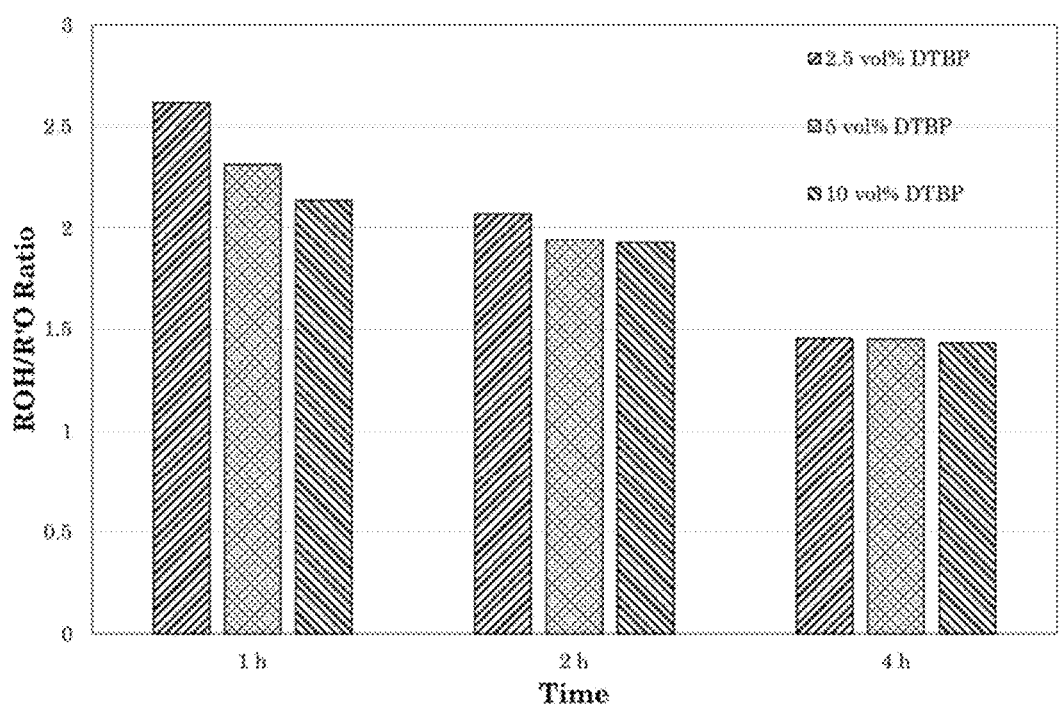
FIG. 15 is a bar chart showing the effect of radical initiator concentration on ROH/R'O ratio. [T: 150° C., P: 3 MPa (30 bar), $y_{O_2,in}$: 0.05, $C_{s-BuMB}$: 3.7 mol %, 15 g sieves].

FIG. 15 shows the results of varying the concentration of the radical initiator, in the range of 2.5 to 10 vol %, on the ratio of alcohols to ketones produced during the oxidation in the presence of sec-butyl metaborate.

In the early stages of the oxidation process, the production of sec-pentanols relative to pentanones is improved the lower the concentration of the radical initiator. As reaction time increased, FIG. 15 shows there was no significant differences in the alcohol-to-ketone ratios within the range of the initiator concentration investigated.

It is proposed that the higher alcohol-to-ketone ratio observed in the early stages of the reaction with 2.5 vol % DTBP initiator may be associated with the lower rate of oxidation, thus limiting the conversion of n-pentane and the undesired consecutive oxidation of the sec-pentanols formed to pentanones.

Molecular Sieves

Figure 16B:
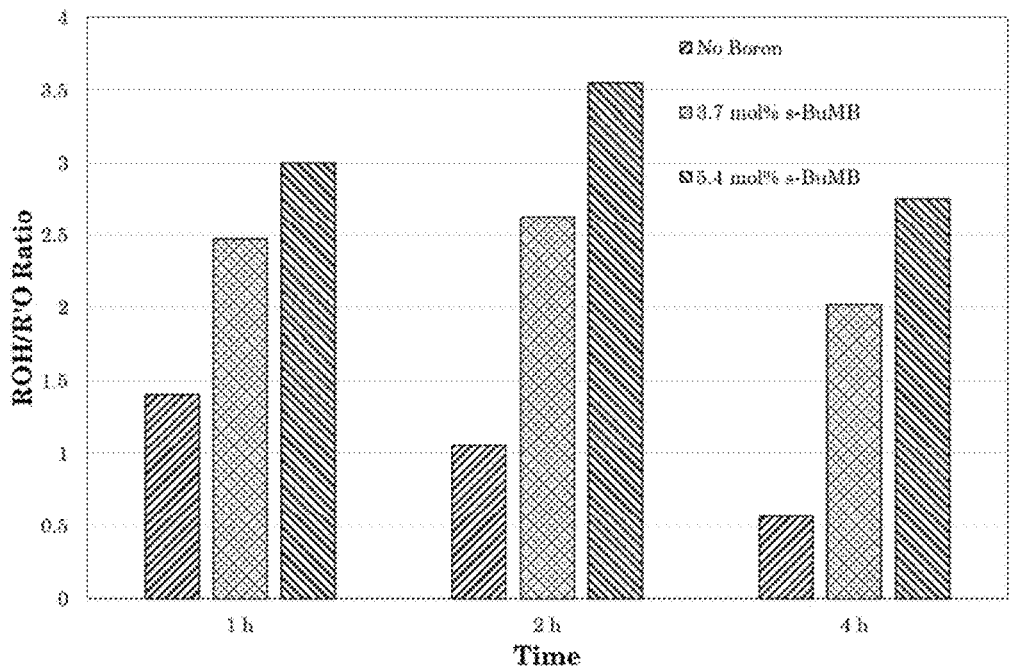

The effect of adsorbents sourced from different suppliers on the oxidation process was investigated by comparing the performance of molecular sieves type 3 Å 4-8 mesh purchased from Honeywell UOP (Sigma-Aldrich, UK) and ACROS Organics (Fisher Scientific, UK). Both adsorbents were activated by drying in an oven at 250° C. prior to use. FIGS. 16(a) and 16(b) shows the results obtained during the oxidation of n-pentane at 150° C. with 3.7 and 5.4 mol % sec-butyl metaborate and 15 g of ACROS Organics molecular sieves.

These experimental runs were carried out under the same conditions as the boron-assisted oxidation results presented in FIG. 6 with the same quantities of UOP type 3 Å molecular sieves, obtained from Sigma-Aldrich. The results in FIG. 16(a) show that the total yields of the oxidation products are lower than for the equivalent experimental runs in FIG. 6 utilizing the same quantity of UOP molecular sieves. For example, for the experiment with 3.7 mol % s-BuMB, total yields of products after 2 hours were 4.14% and 4.65% for the ACROS Organics sieves and UOP sieves, respectively. After 8 hours, the corresponding values were 13.82% and 16.2%. For higher sec-butyl metaborate concentration of 5.4 mol %, the overall yields of oxidation products were 3.69% and 4.59% after 2 hours for the ACROS Organics and UOP sieves, respectively. These results clearly indicate that the UOP molecular sieves exert some catalytic effects on the oxidation process compared to the ACROS Organics molecular sieves. As a result, there was a greater inhibition of the oxidation due to the presence of boron in the case of the runs with the ACROS Organics adsorbents compared with the UOP sieves.

Furthermore, FIG. 16(a) shows that selectivity to sec-pentanols is higher throughout the duration of the reaction for the boron-assisted oxidations with the ACROS Organics sieves than with the UOP sieves shown in FIG. 6. For example, with 3.7 and 5.4 mol % s-BuMB and ACROS Organics sieves, selectivity to sec-pentanols is 47.9 and 55.9% after 2 hours, respectively, compared to 46.4% and 49.4% for the UOP sieves. After 8 hours, the alcohol selectivities decrease to 27.5 and 36.1% for the ACROS Organics adsorbents, while for the UOP sieves the selectivities were 26.3 and 31.7%. In addition, the pentanol-to-pentanone ratios in FIG. 16(b) for the ACROS Organics sieves are significantly higher than for the oxidation runs utilizing the UOP sieves, shown in FIG. 13. Maximum ROH/R'O with the ACROS Organics sieves were obtained after 2 hours, and these correspond to 2.63 and 3.55 for oxidation with 3.7 and 5.4 mol % s-BuMB, respectively. These compare to 2.14 and 2.37% for the same concentrations of boron with the UOP adsorbents, as shown in FIG. 13.

Molecular sieves are synthetic zeolite materials or metal aluminosilicates, with the general chemical formula: $xK_2O \cdot (1-x)Na_2O \cdot Al_2O_3 \cdot 2SiO_2 \cdot nH_2O$, where x is the fraction of potassium ions in the type 3 Å.

Although the exact compositions of each of the molecular sieves discussed above are unknown, the two materials clearly demonstrate catalytic activities on the rate of oxidation, alcohol selectivity and alcohol-to-ketone ratios.

However, these rates are slightly different for each type with the UOP molecular sieves giving a higher yield of oxidation products but lower selectivity to sec-pentanols and lower alcohol-to-ketone ratios compared to the ACROS Organics molecular sieves.

Generally the method of preparation of molecular sieves is the same for different manufacturers. The method involves substitution of Na ions with K ions to make 3 Å molecular sieves.

Without wishing to be bound by theory, it is proposed that the amount of these counter ions (i.e. the extent of substitution) in the resulting molecular sieve composition varies from one manufacturer to another. Typically the amount of K ions in a 3 Å sieve is from 45 to 65%. The remaining counters are Na ions (i.e. are not substituted). Within these ranges, the different amounts of the ions are proposed to effect the performance of the adsorbent.

K ions have smaller pore size than Na ions so may be more effective at trapping water. It is proposed that if the fraction of K ions is at the upper end of the range (i.e. around 65%) then water adsorption efficiency of such a sieve may be much better than a sieve with K ion amount at the lower end of the range (i.e. around 45%). The exact composition of commercially available sieves is often not specified by manufacturers.

REFERENCES

All documents mentioned in this specification are incorporated herein by reference in their entirety.

Arpentinier, P. 2006. "Synthesis of Intermediates for the Petrochemical Industry: Oxidation Processes in Liquid Phase with Oxygen." In Encyclopaedia of Hydrocarbons Vol II: Refining and Petrochemicals, edited by C. Giavarini and F. Trifiro, 636-60. Roma: ENI: Istituto Della Enciclopedia Italiana.

Bashkirov, A. N., and V. V. Kamzolkin. 1959. "Synthesis of Higher Aliphatic Alcohols by Direct Oxidation of Paraffinic Hydrocarbons." In Proc. 5th World Pet. Cong., Sec. IV, Paper 15, 175-183. New York: World Petroleum Congress.

Bashkirov, A. N., V. V. Kamzolkin, K. M. Sokova, and T. P. Andreyeva. 1965. "The Mechanism of the Liquid-Phase Oxidation of Paraffinic Hydrocarbons." In The Oxidation of Hydrocarbons in the Liquid Phase, edited by N. M. Emanuel', 183-93. Oxford: Pergamon Press Ltd.

Bashkirov, A. N., V. V. Kamzolkin, K. M. Sokova, T. P. Andreyeva, V. V. Korneva, and L. I. Zakharkin. 1961. "The Production of Cyclododecanol by the Liquid-Phase Oxidation of Cyclododecane." Neftekhimiya 1 (4): 527-34.

Beckett, M. A., M. P. Rugen-Hankey, G. C. Strickland, and K. S. Varma. 2001. "Lewis Acidity in Haloalkyl Orthoborate and Metaborate Esters." Phosphorus, Sulfur Silicon Relat. Elem. 169 (1): 113-16.

Beckett, M. A., G. C. Strickland, J. R. Holland, and K. S. Varma. 1996. "A Convenient N. M. R. Method for the Measurement of Lewis Acidity at Boron Centres: Correlation of Reaction Rates of Lewis Acid Initiated Epoxide Polymerizations with Lewis Acidity." Polymer 37 (20): 4629-31.

Freund, M., R. Csikós, S. Keszthelyi, and Gy. Mózes. 1982. "Paraffin Products: Properties, Technologies, Applications." In Dev. Petrol. Sci., Vol. 14, edited by Gy. Mózes, 13-70. Amsterdam: Elsevier.

Griesbaum, K., A. Behr, D. Biedenkapp, H-W. Voges, D. Garbe, C. Paetz, G. Collin, D. Mayer, and H. Hoke. 2012. "Hydrocarbons." Ullmann's Encyclopedia of Industrial Chemistry. Wiley-VCH Verlag GmbH & Co. KGaA, Weinheim.

Kijeiski, J., and A. Baiker. 1989. "Acidic Sites on Catalyst Surfaces and Their Determination." Catal. Today 5 (1): 1-120.

Labinger, J. A., and J. E. Bercaw. 2002. "Understanding and Exploiting C—H Bond Activation." Nature 417 (6888): 507-14.

Lappe, P., and T. Hofmann. 2011. "Pentanols." Ullmann's Encyclopaedia of Industrial Chemistry. Weinheim: Wiley-VCH Verlag GmbH & Co. KGaA.

Lappert, M. F. 1956. "Organic Compounds of Boron." Chem. Rev. 56 (5): 959-1064.

Lappert, M. F. 1958a. "Cyclic Organic Boron Compounds. Part I. Preparation, Characterisation, and Stability of Esters of Metaboric Acid." J. Chem. Soc., no. 2790: 2790-93.

Lappert, M. F. 1958b. "Cyclic Organic Boron Compounds. Part II. Chemical Properties of N-Butyl Metaborate." J. Chem. Soc., 3256-59.

Lundeen, A., and R. L. Poe. 1977. "Alpha-Alcohols." In Encyclopedia of Chemical Processing and Design: Volume 2—Additives to Alpha, edited by J. J. McKetta and W. A. Cunningham. New York: Marcel Dekker, Inc.

Matar, S., and L. F. Hatch. 2000. Chemistry of Petrochemical Processes. 2nd ed. Houston: Gulf Publishing.

Mushenko, D. V., and R. D. Dergacheva. 1961. "The Production of Secondary Amyl Alcohols." Neftekhimiya 1 (6): 811-16.

Sakaguchi, H., Y. Kamiya, and N. Ohta. 1972. "Autoxidation of Hydrocarbons in the Presence of Boric Acids Decomposition of Aromatic Hydroperoxides." Bull. Jap. Pet. Inst. 14 (1): 71.

Sheldon, R. A., and J. A. van Doom. 1974. "Boron-Catalysed Epoxidation of Olefins with Tert-Butyl Hydroperoxide." J. Catal. 34: 242-45.

Shilov, A. E., and G. B. Shul'pin. 2000. Activation and Catalytic Reactions of Saturated Hydrocarbons in the Presence of Metal Complexes. Dordrecht: Kluwer Academic Publishers.

Sivaev, I. B., and V. I. Bregadze. 2014. "Lewis Acidity of Boron Compounds." Coord. Chem. Rev. 270: 75-88.

Teles, J. H., I. Hermans, G. Franz, and R. A. Sheldon. 2015. "Oxidation." Ullmann's Encyclopedia of Industrial Chemistry. Wiley-VCH Verlag GmbH & Co. KGaA, Weinheim.

Weissermel, K., and H.-J. Arpe. 1997. Industrial Organic Chemistry. 3rd ed. Weinheim: Wiley-VCH.

Woods, W. G., and R. J. Brotherton. 1970. "Oxidations of Organic Substrates in the Presence of Boron Compounds." In Progress in Boron Chemistry, edited by R. J. Brotherton and H. Steinberg, Vol. 3, 1-115. Pergamon Press, Oxford, UK.

Claimed is:

1. A method for oxidation of $C_{1-9}$-alkanes, the method comprising:
   providing a mixture of:
      a $C_{1-9}$-alkane in a liquid phase;
      a boron containing reagent;
      a free radical initiator; and
      a drying means; and,
   performing an oxidation reaction at a temperature from 130° C. to 180° C. in the presence of oxygen.

2. The method of claim 1 wherein the mixture is at a pressure from 2 to 5 MPa.

3. The method of claim 2 wherein the pressure is from 2 to 3 MPa.

4. The method of claim 1, wherein the boron containing reagent is a borate ester.

5. The method of claim 4 wherein the borate ester is a metaborate ester.

6. The method of claim 1 wherein an amount of boron containing reagent is from 1 to 10 mol % with respect to an amount of alkane.

7. The method of claim 1 wherein the free radical initiator is a peroxide.

8. The method of claim 7 wherein the peroxide is a dialkyl peroxide.

9. The method of claim 8 wherein the dialkyl peroxide is di-tert-butyl peroxide.

10. The method of claim 1 wherein the drying means is a drying agent.

11. The method of claim 10 wherein the drying agent is a molecular sieve.

12. The method of claim 11 wherein the molecular sieves are 3 Å molecular sieves.

13. The method of claim 1 wherein the drying means is a semi-permeable membrane.

14. The method of claim 13 wherein the semi-permeable membrane is a hydrophilic pervaporation membrane.

15. The method of claim 1 wherein the drying means is a combination of a drying agent and a semi-permeable membrane.

16. The method of claim 1 wherein the oxygen comprises a mixture of oxygen and nitrogen gases.

17. The method of claim 16 wherein the mixture of oxygen and nitrogen gases contains from about 1 to 10 vol % oxygen.

18. The method of claim 1 wherein the temperature is between 130° C. and 150° C.

19. The method of claim 18 wherein the mixture is maintained at the temperature between 130° C. and 150° C. for 0.5 to 8 hours.

20. The method of claim 1 wherein the alkane is pentane.

21. The method of claim 20 wherein the pentane is n-pentane.

22. The method of claim 1 further comprising:
   a hydrolysis step in which a borate ester produced during the oxidation reaction is treated with water to produce an alcohol.

23. The method of claim 1 further comprising:
   a conversion step in which an alcohol produced during the oxidation reaction is converted to an olefin, an ester, an ether or a higher molecular weight product.

24. The method of claim 23 wherein prior to the conversion step, the alcohol is recovered from the oxidation reaction by hydrolysis.

25. The method of claim 1 further comprising:
   a conversion step wherein borate ester produced during the oxidation reaction is converted directly to an olefin by thermal decomposition at a temperature of at least 300° C.

26. The method of claim 1 further comprising:
   a step of recovering unreacted alkane from the reaction mixture after the oxidation reaction.

27. A composition for oxidation of $C_{1-9}$-alkanes to sec-$C_{1-9}$-alcohols, the composition comprising:
   a $C_{1-9}$-alkane in a liquid phase;
   a boron containing reagent;
   a free radical initiator; and
   a drying agent.

* * * * *